US012329737B2

(12) United States Patent
Baker et al.

(10) Patent No.: US 12,329,737 B2
(45) Date of Patent: Jun. 17, 2025

(54) ***DENDRILLA MEMBRANOSA* COMPOUNDS, DERIVATIVES THEREOF, AND USES THEREOF**

(71) Applicants: UNIVERSITY OF SOUTH FLORIDA, Tampa, FL (US); THE UAB RESEARCH FOUNDATION, Birmingham, AL (US)

(72) Inventors: Bill J. Baker, Temple Terrace, FL (US); Lindsey N. Shaw, Tampa, FL (US); Andrew Jason Shilling, Tampa, FL (US); Alexandre Jean Bory, Yvonand (CH); Jessie Allen (Adams), Tampa, FL (US); Charles Dunkle Amsler, Jr., Pelham, AL (US); James Bruce McClintock, Birmingham, AL (US)

(73) Assignees: UNIVERSITY OF SOUTH FLORIDA; THE UAB RESEARCH FOUNDATION

( * ) Notice: Subject to any disclaimer, the term of this patent is extended or adjusted under 35 U.S.C. 154(b) by 0 days.

(21) Appl. No.: 18/152,098

(22) Filed: Jan. 9, 2023

(65) Prior Publication Data
US 2023/0165830 A1 Jun. 1, 2023

Related U.S. Application Data

(63) Continuation of application No. 16/715,447, filed on Dec. 16, 2019, now Pat. No. 11,547,691.

(60) Provisional application No. 62/779,944, filed on Dec. 14, 2018.

(51) Int. Cl.
*A61K 31/343* (2006.01)
*A61K 31/192* (2006.01)
*A61K 31/352* (2006.01)

(52) U.S. Cl.
CPC .......... *A61K 31/343* (2013.01); *A61K 31/192* (2013.01); *A61K 31/352* (2013.01); *A61K 2236/39* (2013.01)

(58) Field of Classification Search
CPC .................................................. A61K 31/343
See application file for complete search history.

(56) References Cited

U.S. PATENT DOCUMENTS

| | | | |
|---|---|---|---|
| 5,929,124 A | 7/1999 | Hostettmenn et al. | |
| 9,872,849 B2 * | 1/2018 | Baker | A61K 31/366 |
| 11,213,507 B2 * | 1/2022 | Baker | A61K 9/0014 |
| 11,547,691 B1 * | 1/2023 | Baker | A61K 31/343 |

FOREIGN PATENT DOCUMENTS

| | | |
|---|---|---|
| CN | 102125042 B | 7/2013 |
| CN | 104829664 B | 7/2017 |
| WO | 2017177142 A1 | 10/2017 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Lebeaux, Microbiology and Molecular Biology Reviews, Sep. 2014 vol. 78 Issue 3, 1-542.*
Pulti, Acta Crystallographia Section C, 1993, 1373-1376.*
Baker, B. J., et al. "Chemical and ecological studies of the Antarctic sponge *Dendrilla membranosa*." Journal of Natural Products 58.9 (1995): 1459-1462.
Buckleton, J. S., et al. "Structure of tetrahydroaplysulphurin-1." Acta Crystallographica Section C: Crystal Structure Communications 43.12 (1987): 2430-2432.
Di'az-Marrero, A. R., et al. "Conformational analysis and absolute stereochemistry of 'spongian'-related metabolites." Tetrahedron 60.5 (2004): 1073-1078.
Graham, S. K., et al. "The absolute structure of (+)-aplysulfurin." Journal of Chemical Crystallography 40.5 (2010): 468-471.
Karuso, P., et al. "Terpenoid constituents of morphologically similar sponges in the family Aplysillidae." Australian journal of chemistry 39.10 (1986): 1643-1653.
Karuso, P., et al. "The constituents of marine sponges. I. The isolation from Aplysilla sulphurea (Dendroceratida) of (1R*, 1'S*, 1'R*, 3R*)-1-acetoxy-4-ethyl-5-(1, 3, 3-trimethylcyclohexyl)-1, 3-dihydroisobenzofuran-1'(4), 3-carbolactone and the determination of its crystal structure." Australian journal of chemistry 37.5 (1984): 1081-1093.
Keyzers, R. A., et al. "Novel anti-inflammatory spongian diterpenes from the New Zealand marine sponge *Chelonaplysilla violacea*." European Journal of Organic Chemistry Feb. 2004 (2004): 419-425.
Laport, M. S., et al. "Marine sponges: potential sources of new antimicrobial drugs." Current pharmaceutical biotechnology 10.1 (2009): 86-105.
Mayer, Ams, et al. "Marine pharmacology in Apr. 2003: Marine compounds with anthelmintic antibacterial, anticoagulant, antifungal, anti-inflammatory, antimalarial, antiplatelet, antiprotozoal, antituberculosis, and antiviral activities; affecting the cardiovascular, immune and nervous systems, and other miscellaneous mechanisms of action." Comparative Biochemistry and Physiology Part C: Toxicology & Pharmacology 145.4 (2007): 553-581.

(Continued)

*Primary Examiner* — Nizal S Chandrakumar
(74) *Attorney, Agent, or Firm* — Quarles & Brady LLP

(57) ABSTRACT

Described herein are *Dendrilla membranosa* compounds and derivatives thereof. Also described herein are formulations that can contain an amount of one or more *Dendrilla membranosa* compounds or derivatives thereof and a carrier. Also described herein are methods of administering one or more *Dendrilla membranosa* compound and/or derivative thereof or a formulation thereof to a subject in need thereof.

6 Claims, 2 Drawing Sheets

(56) References Cited

OTHER PUBLICATIONS

Mayol, L.; et al. New Degraded Diterpenes from the Sponge *Spongionella gracilis*. Gazzetta Chim. Ital. 1988, 118, 559-563.
Molinski, T.F. et al. "Metabolites of the antarctic sponge *Dendrilla membranosa*." The Journal of Organic Chemistry 52.2 (1987): 296-298.
Pellaud, S., et al. "Wrinkled 1 and Acyl-Coa: Diacylglycerol Acyltransferase 1 regulate tocochromanol metabolism in *Arabidopsis*." New Phytologist 217.1 (2018): 245-260.
Tischler, M., et al. "Glaciolide, a degraded diterpenoid with a new carbon skeleton from the nudibranch *Cadlina luteomarginata* and the sponge *Aplysilla glacialis*." Tetrahedron letters 30.42 (1989): 5717-5720.
Von Salm et al., "Darwinolide, a new diterpene scaffold that inhibits methicillin-resistant *Staphylococcus aureus* biofilm from the Antarctic sponge *Dendrilla membranosa*." Organic letters 18.11 (2016): 2596-2599.
Ankisetty et al., "Further Membranolide Diterpenes from the Antarctic Sponge *Dendrilla membranosa*." Journal of natural products 67.7 (2004): 1172-1174.

\* cited by examiner

DENDRILLA MEMBRANOSA COMPOUNDS, DERIVATIVES THEREOF, AND USES THEREOF

CROSS-REFERENCE TO RELATED APPLICATIONS

This application is a continuation of U.S. patent application Ser. No. 16/715,447, filed Dec. 16, 2019, now U.S. Pat. No. 11,547,691, and claims the benefit of and priority to U.S. Provisional Patent Application No. 62/779,944, filed on Dec. 14, 2018, the contents of each which are incorporated by reference herein in their entireties.

STATEMENT REGARDING FEDERALLY SPONSORED RESEARCH

This invention was made with Government support PLR-1341339 awarded by the National Science Foundation. The Government has certain rights in the invention.

BACKGROUND

Biofilms are formed by all bacterial species, and are a collection of cells coated in an extracellular matrix composed of polysaccharides, proteins, and DNA. In the context of disease, biofilms are the driving force behind many kinds of chronic infection, including, but not limited to, urinary tract infections, upper respiratory infections, and periodontitis. Further, biofilms commonly form on implanted medical devices, such as catheters, artificial joints, pacemakers, pins, and plates. Estimates suggest that up to 80 percent of all infections are believed to be caused by bacterial biofilms, making them a serious public health concern. Intervention strategies targeting biofilms, including multi-drug resistant, has the potential to save numerous lives and significantly limit morbidity resulting from bacterial infection. There is therefore an urgent and desperate need for the development of molecules that can actively impact cell viability within biofilms.

SUMMARY

Described herein are *Dendrilla membranosa* compounds and derivatives thereof. Also described herein are formulations that can contain an amount of one or more *Dendrilla membranosa* compounds or derivatives thereof and a carrier. Also described herein are methods of administering one or more *Dendrilla membranosa* compound and/or derivative thereof or a formulation thereof to a subject in need thereof.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
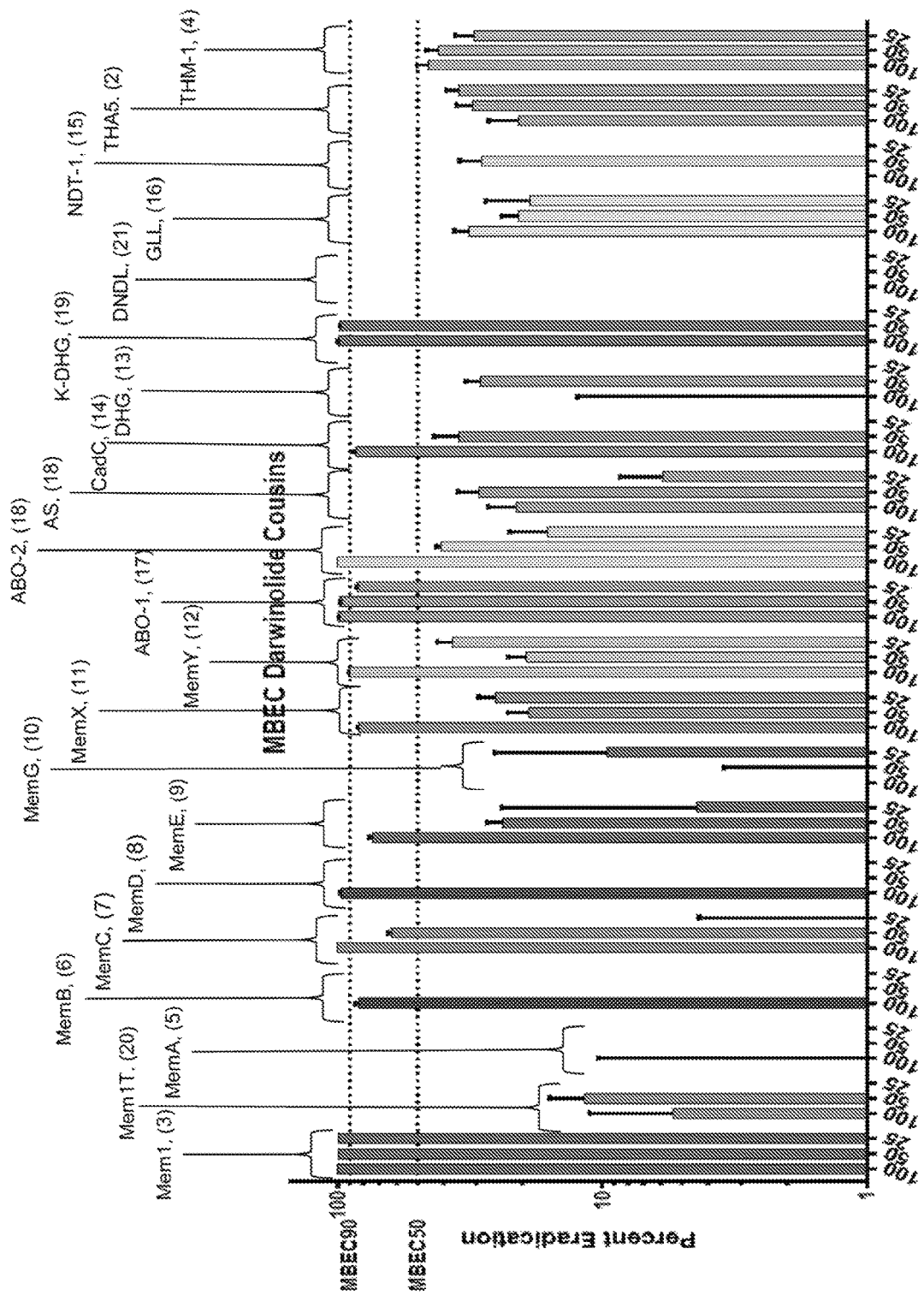
FIG. 1 shows a graph that can demonstrate the minimum biofilm eradication concentration (MBEC) of various compounds against multidrug resistant *S. aureus* at varying concentrations represented as percent eradication. Each sample tested in triplicate for all concentrations. Calculated based on no drug controls and represented as a log 10 scale. Error=±SEM. MBEC 90/50: level to which 90% or 50% of the population was eradicated compared to no treatment.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, organic chemistry, biochemistry, physiology, cell biology, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary.

It is also to be understood that the terminology used herein is for purposes of describing particular embodiments only, and is not intended to be limiting. It is also possible in the present disclosure that steps can be executed in different sequence where this is logically possible unless the context clearly dictates otherwise.

Definitions

As used herein, "active agent" or "active ingredient" refers to a substance, compound, or molecule that is biologically active or otherwise, induces a biological or physiological effect on a subject to which it is administered to. In other words, "active agent" or "active ingredient" refers to a component or components of a composition to which the whole or part of the effect of the composition is attributed.

As used herein, "administering" refers to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques.

As used herein, "agent" refers to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

The term "biocompatible", as used herein, refers to a material that along with any metabolites or degradation products thereof that are generally non-toxic to the recipient and do not cause any significant adverse effects to the recipient. Generally speaking, biocompatible materials are materials that do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

As used herein, "control" refers to an alternative subject or sample used in an experiment for comparison purpose and included to minimize or distinguish the effect of variables other than an independent variable.

The term "copolymer" as used herein, generally refers to a single polymeric material that is comprised of two or more different monomers. The copolymer can be of any form, such as random, block, graft, etc. The copolymers can have any end-group, including capped or acid end groups.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "dose," "unit dose," or "dosage" refers to physically discrete units suitable for use in a subject, each unit containing a predetermined quantity of the compound(s) described herein and/or a pharmaceutical formulation thereof calculated to produce the desired response or responses in association with its administration.

As used herein, "effective amount" refers to the amount of a compound provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function. The "effective amount" can refer to the amount of a *Dendrilla membranosa* compound and/or derivative thereof or a formulation thereof described herein that can be antibacterial and/or antibiofilm. The "effective amount" can be the amount effective to kill a bacterial cell, inhibit or reduce the growth of a bacterial cell, and/or reduce or inhibit the pathogenicity of a bacterial cell. The "effective amount" can be the amount effective to kill a bacterial cell encapsulated in a biofilm, inhibit or reduce the growth of a bacterial cell encapsulated in a biofilm, and/or reduce or inhibit the pathogenicity of a bacterial cell encapsulated in a biofilm. The "effective amount" can refer to the amount effective to treat or prevent a *Staphylococcus* infection. The "effective amount" can refer to the amount effective to treat or prevent a *Staphylococcus aureus* infection. The "effective amount" can refer to the amount effective to treat or prevent a methicillin-resistant *Staphylococcus* infection.

The term "hydrophilic", as used herein, refers to substances that have strongly polar groups that are readily soluble in water.

The term "hydrophobic", as used herein, refers to substances that lack an affinity for water; tending to repel and not absorb water as well as not dissolve in or mix with water.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "positive control" refers to a "control" that is designed to produce the desired result, provided that all reagents are functioning properly and that the experiment is properly conducted.

As used interchangeably herein, the terms "sufficient" and "effective," can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a bacterial infection and/or a biofilm. The effect can be therapeutic in terms of a partial or complete cure of a disease, condition, symptom or adverse effect attributed to the disease, disorder, or condition. The term "treatment" as used herein covers any treatment of as a bacterial infection and/or a biofilm, in a subject, particularly a human subject, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, halo, hydroxy, alkylthio, arylthio, alkoxy, aryloxy, amino, mono- or di-substituted amino, ammonio or substituted ammonio, nitroso, cyano, sulfonato, mercapto, nitro, oxo, alkyl, alkenyl, cycloalkyl, benzyl, phenyl, substituted benzyl, substituted phenyl, benzylcarbonyl, phenylcarbonyl, saccharides, substituted benzylcarbonyl, substituted phenylcarbonyl and phosphorus derivatives. The aryl group can include two or more fused rings, where at least one of the rings is an aromatic ring. Examples include naphthalene, anthracene, and other fused aromatic compounds.

The term "alkoxy group" as used herein is represented by the formula —OR, where R is an alkyl group or aryl group as defined herein.

The term "acyl group" as used herein is represented by the formula —C(O)R, where R is hydrogen, an alkyl group, or aryl group as defined herein.

The term "substantially" as used herein with respect to stereochemistry is defined as having an enantiomeric excess of greater than 80%, greater than 85%, greater than 90%, greater than 95%, greater than 99%, or 100% of a particular enantiomer.

The term "oxo group" as used herein is represented by the formula =O.

Discussion

Biofilms are formed by all bacterial species, and are a collection of cells coated in an extracellular matrix composed of polysaccharides, proteins, and DNA. In the context of disease, biofilms are the driving force behind many kinds of chronic infection, including, but not limited to, urinary tract infections, upper respiratory infections, and periodontitis. Further, biofilms commonly form on implanted medical devices, such as catheters, artificial joints, pacemakers, pins, and plates. Estimates suggest that up to 80 percent of all infections are believed to be caused by bacterial biofilms, making them a serious public health concern. Intervention strategies targeting biofilms, including multi-drug resistant, has the potential to save numerous lives and significantly limit morbidity resulting from bacterial infection.

Additionally, resistance mechanisms have rendered many antibiotics ineffective while drug discovery efforts of the industry have turned to more profitable targets, leading to the concerns of the World Health Organization which now describes the problem as one of the three major medical threats of the $21^{st}$ century.

There is therefore an urgent and desperate need for the development of molecules that can actively impact cell viability within biofilms as well as those that can impact the cell viability of drug resistant bacterial cells, including but not limited to, those bacteria with multi-drug resistance.

With that said, described herein are compounds and formulations thereof that can be capable of killing and/or inhibiting the growth of a bacterial cell. In some embodiments, the bacterial cell can be contained within a biofilm. Also described herein are methods of treating a bacterial infection in a subject that can include the method of administering one or more of the compounds described herein or a formulation thereof to a subject in need thereof. In some embodiments, the bacterial infection is caused by a multidrug resistant bacterial strain. In some embodiments, the bacterial infection is caused by a drug resistant bacterial strain. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

*Dendrilla membranosa* Compounds and Derivatives Thereof

As generally discussed above, described herein are compounds isolated from *Dendrilla membranosa* and synthetic derivatives thereof. In one embodiment, the compounds and derivatives thereof have the structure I

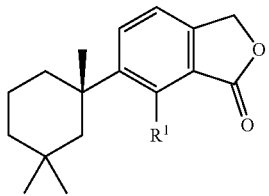

I wherein $R^1$ is hydrogen, an alkyl group, an alkoxy group, an aryl group, or an acyl group.

In one embodiment, the compound or derivative thereof has the structure V,

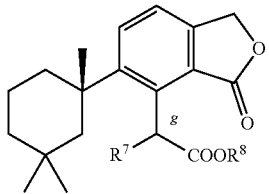

V wherein $R^7$ and $R^8$ are each a $C_1$ to $C_5$ alkyl group, and the stereochemistry at carbon g is substantially R, substantially S, or racemic. In another embodiment, $R^7$ and $R^8$ of structure V are each a methyl group. In another embodiment, $R^7$ and $R^8$ are each a methyl group of structure V, and the stereochemistry at carbon g is substantially R, which is also referred to herein as Membranolide. The Examples provide non-limiting procedures for making compounds having the structures I and V, where a number of $R^1$ groups can be coupled to the aromatic ring of structure I using standard organic coupling techniques.

In one embodiment, the compounds and derivatives thereof have the structure II

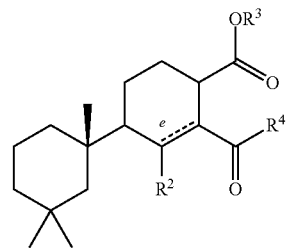

II wherein $R^2$, $R^3$, and $R^4$ are, independently, hydrogen, an alkyl group, an alkoxy group, an aryl group, or an acyl group; and bond e is present or not present.

In one embodiment, the compound or derivative thereof has the structure II, wherein $R^3$ is a $C_1$ to $C_5$ alkyl group, $R^4$ is hydrogen or a $C_1$ to $C_5$ alkyl group, and bond e is present. In another embodiment, the compound or derivative thereof has the structure II, wherein $R^2$ is an oxo group, $R^3$ is a $C_1$ to $C_5$ alkyl group, $R^4$ is hydrogen or a $C_1$ to $C_5$ alkyl group, and bond e is present.

In another embodiment, the compound or derivative thereof has the structure VI

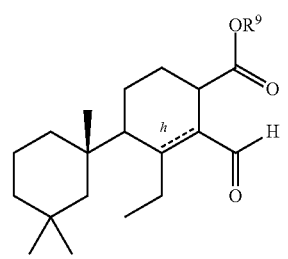

VI wherein $R^9$ is a $C_1$ to $C_5$ alkyl group, and bond h is present or absent.

In another embodiment, $R^9$ in structure VI is a methyl group. In another embodiment, $R^9$ in structure VI is a methyl group and bond h is present, which is referred to herein as ABO-1. In one embodiment, ABO-1 can be modified using techniques known in the art to vary $R^2$, $R^3$, and $R^4$ in structure II to produce a number of different derivatives.

In one embodiment, the compounds and derivatives thereof have the structure III

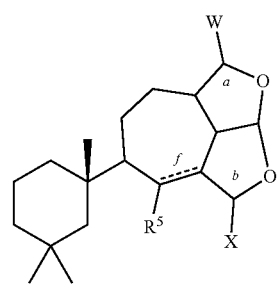

III wherein $R^5$ is hydrogen, an alkyl group, an alkoxy group, an aryl group, or an acyl group; W and X are, independently, an oxo group or $OR^6$, where $R^6$ is hydrogen, an alkyl group, an aryl group, or an acyl group; and wherein when W or X is OR$^6$, the stereochemistry at carbons a and b is substantially R, substantially S, or racemic; and bond f is present or not present.

In another embodiment, the compound or derivative thereof is structure III, wherein R$^5$ is a C$_1$ to C$_5$ alkyl group, W is an acyl group, X is an oxo group, bond f is present, and the stereochemistry at carbon a is substantially R, substantially S, or racemic. In another embodiment, the compound or derivative thereof is structure VII,

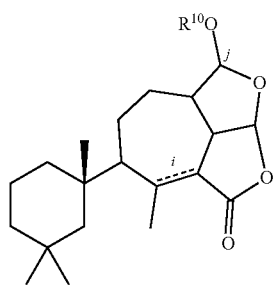

VII wherein R$^{10}$ is C(O)R$^{20}$, wherein R$^{20}$ is a C$_1$ to C$_5$ alkyl group, bond i is present or absent, and the stereochemistry at carbon j is substantially R, substantially S, or racemic. In another embodiment, R$^{10}$ is C(O)Me in structure VII and bond i is present. In another embodiment, R$^{10}$ in structure VII is C(O)Me, bond i is present, and the stereochemistry at carbon j is substantially S, which is referred to herein as Darwinolide. In one embodiment, Darwinolide can be modified using techniques known in the art to vary R$^5$, W, and X in structure III to produce a number of different derivatives.

In one embodiment, the compounds and derivatives thereof have the structure IV

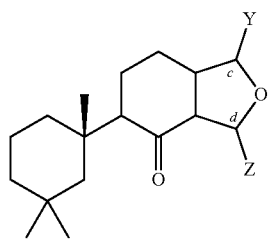

IV

Wherein Y and Z are, independently, an oxo group or OR$^6$, where R$^6$ is hydrogen, an alkyl group, an aryl group, or an acyl group; and wherein when Y or Z is OR$^6$, the stereochemistry at carbons a, b, c, and d is substantially R, substantially S, or racemic.

In one embodiment, the compound or derivative thereof is formula IV, wherein Y and Z are each an acyl group, and the stereochemistry at carbons c and d is substantially R, substantially S, or racemic. In another embodiment, the compound or derivative thereof has structure VIII, 1.

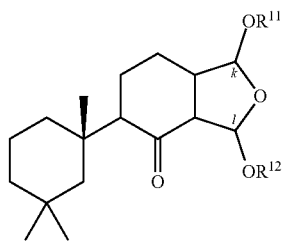

VIII wherein R$^{11}$ and R$^{12}$ are each C(O)R$^{20}$, wherein R$^{20}$ is a C$_1$ to C$_5$ alkyl group, and the stereochemistry at carbons k and l is substantially R, substantially S, or racemic. In another embodiment, R$^{11}$ and R$^{12}$ in structure VIII are each C(O)Me. In another embodiment, R$^{11}$ and R$^{12}$ in structure VIII are each C(O)Me, the stereochemistry at carbon k is substantially S, and the stereochemistry at carbon l is substantially R, which is referred to herein as Keto-DHG. Organic techniques known in the art can be used to produce compounds having the structures IV and VIII.

In one embodiment, 9,11-dihydrogracilin, which is a compound produced by *Dendrilla membranosa*, can be treated by ozonolysis to produce the oxo compound of structures IV and VIII. Standard organic techniques can be used to vary the Y and Z groups as well.

In some embodiments, the compounds isolated from *Dendrilla membranosa* can have a structure according to any of compounds (10), (12), (17) or (23).

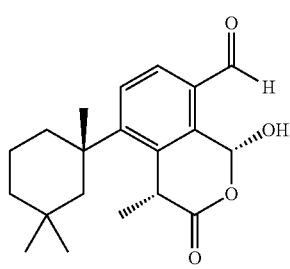

(10)

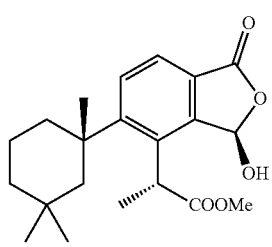

(12)

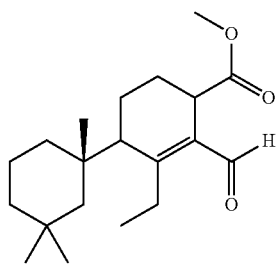

(17)

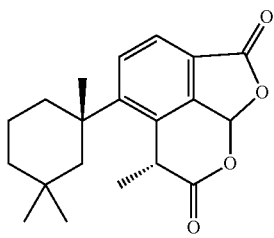
(23)
In some embodiments, the compounds can be a synthetic or semisynthetic derivative from a compound that can be isolated from *Dendrilla membranosa*. In some embodiments, the derivative can have a structure according to (8), (9), (11), or (18)
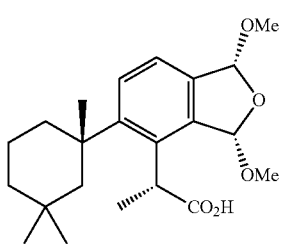
(8)
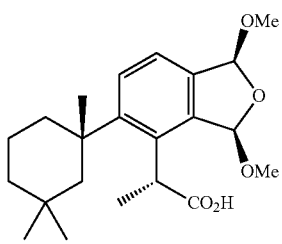
(9)
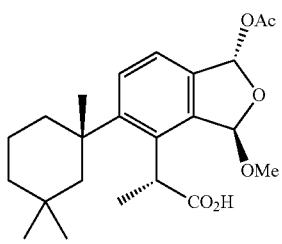
(11)
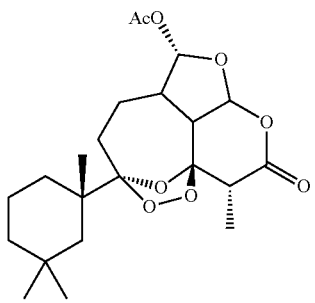
(18)
In another embodiment, the *Dendrilla membranosa* compounds and derivatives thereof can include any of compounds 1-24.
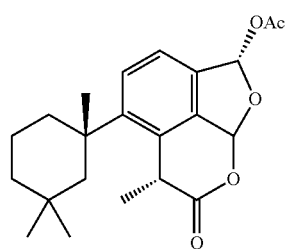
(1)
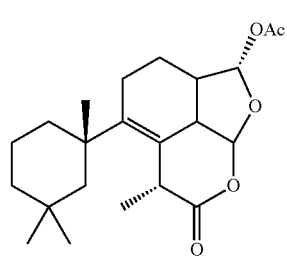
(2)
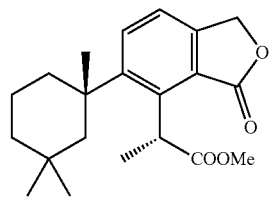
(3)
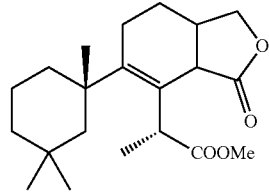
(4)
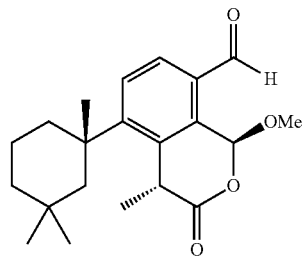
(5)
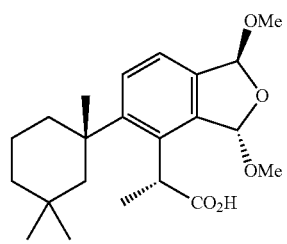
(6)

(7) 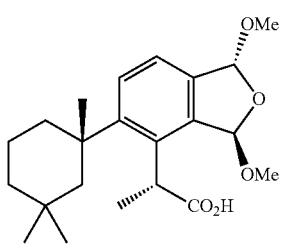
(8) 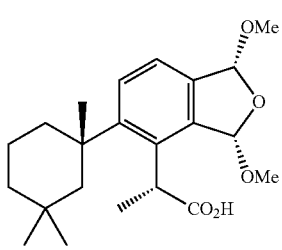
(9) 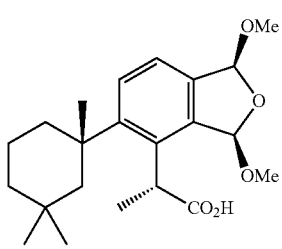
(10) 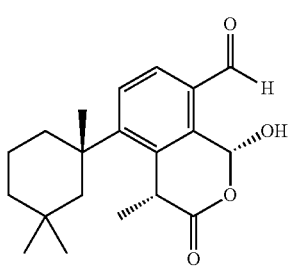
(11) 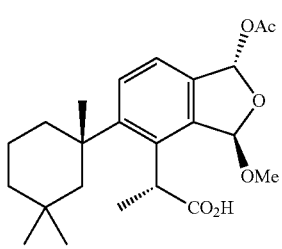
(12) 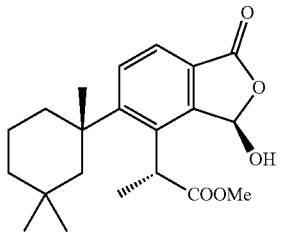
(13) 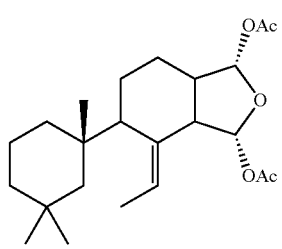
(14) 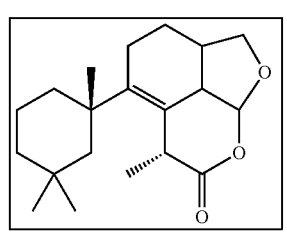
(15) 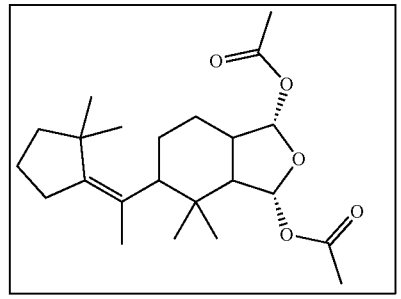
(16) 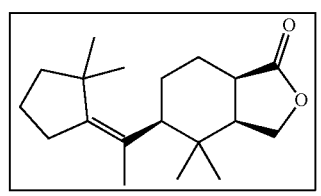
(17) 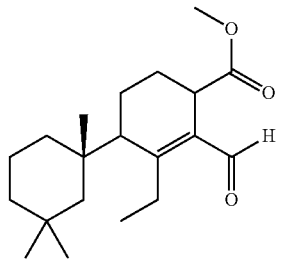
(18) 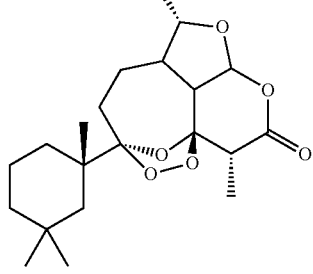

(19)
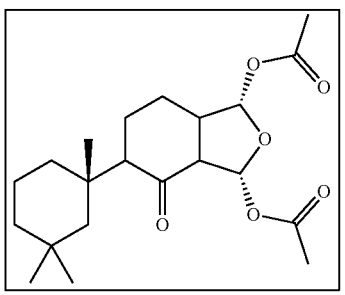

(20)
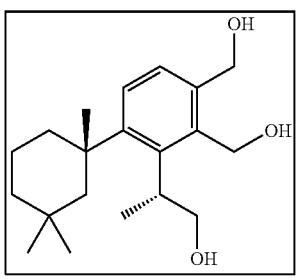

(21)
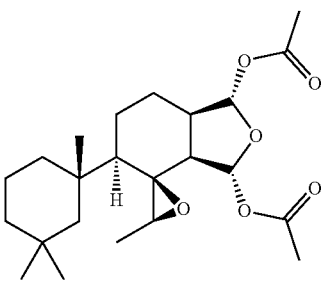

(22)
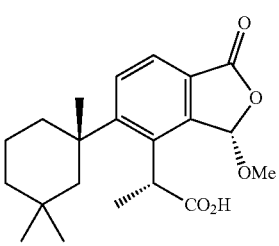

(23)
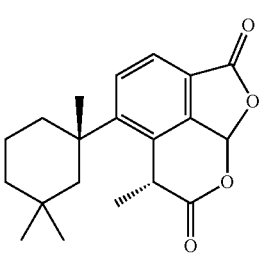

(24)
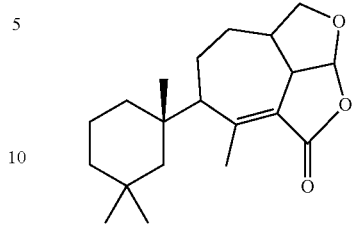

The compounds produced by *Dendrilla membranosa* and derivatives thereof can be antibacterial. As used herein, "antibacterial" can refer to the ability of a compound or formulation to kill a bacterial cell, reduce and/or inhibit the growth of a bacterial cell, and/or reduce or inhibit the pathogenicity of a bacterial cell. The compounds can be antibiofilm. As used herein, "antibiofilm" can refer to the ability of a compound or formulation to reduce the amount of biofilm, to kill a bacterial cell within a biofilm, reduce and/or inhibit the growth of a bacterial cell within a biofilm, and/or reduce or inhibit the pathogenicity of a bacterial cell within a biofilm.

In one embodiment, the methods and compositions described herein can kill both Gram-negative bacteria and Gram-positive bacteria. Examples of Gram-negative bacteria include, but not limited to, *E. coli, Klebsiella, Enterobacter, H. influenzae, Proteus, Serratia, Pseudomonas* species, or any combination thereof. Examples of Gram-positive bacteria include, but not limited to methicillin-resistant *Staphylococcus aureus*, a staphylococcal species, or a streptococcal species. In another embodiment, the bacteria can include an anaerobe such as a *Clostridium* species, a Peptococcus species, a *Bacteroides* species, or Mycobacteriaceae alone or in combination with Gram-positive and/or Gram-negative bacteria.

Formulations of the *Dendrilla membranosa* Compounds and Derivatives Thereof

Also described herein are formulations that can contain one or more *Dendrilla membranosa* compounds and derivatives thereof described herein and a suitable carrier. The carrier can be a pharmaceutically acceptable carrier. The formulation can be a pharmaceutical formulation. In one embodiment, the formulation can include one or more compounds produced by *Dendrilla membranosa* and one or more derivatives of a compound produced by *Dendrilla membranosa*. In one embodiment, the formulation can include one or more compounds having the structure I with one or more compounds having the structure II, III, and/or IV. In one embodiment, the formulation can include one or more compounds having the structure II with one or more compounds having the structure I, III, and/or IV. In one embodiment, the formulation can include one or more compounds having the structure III with one or more compounds having the structure I, II, and/or IV. In one embodiment, the formulation can include one or more compounds having the structure IV with one or more compounds having the structure I, II, and/or III.

In some embodiments, the amount of the *Dendrilla membranosa* compounds and/or derivatives thereof can be an effective amount. In some embodiments, one or more of the *Dendrilla membranosa* compounds and/or derivatives thereof or any formulation thereof described herein can have a MBEC ranging from about 25 µg/mL to about 100 µg/mL.

In some embodiments, one or more of the *Dendrilla membranosa* compounds and/or derivatives thereof or any formulation thereof described herein can have a MIC of ranging from about 25 μg/mL to about 100 μg/mL.

The compounds and/or formulations described herein can be administered to a subject. The subject can be infected with one or more bacteria. The bacteria can be pathogenic bacteria. The bacteria can be encapsulated within a biofilm. The subject can be a subject in need thereof. The compounds and formulations described herein can be administered by a suitable route, such as but not limited to oral, infusion, and intravenous. Other suitable routes are described elsewhere herein.

Parenteral Formulations

The *Dendrilla membranosa* compounds and derivatives thereof described herein can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the *Dendrilla membranosa* compounds and derivatives thereof described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine.

Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the *Dendrilla membranosa* compounds and derivatives thereof.

The formulation can be buffered to a pH of 3-8 for parenteral administration upon reconstitution. In some aspects, the pH of the formulation can be a pH of about 7.0-7.4 upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the *Dendrilla membranosa* compounds and/or derivatives thereof in the desired amount in the appropriate solvent or dispersion medium with one or more of the excipients listed above, as required, followed by filtered sterilization. Dispersions can be prepared by incorporating the various sterilized *Dendrilla membranosa* compounds and/or derivatives thereof into a sterile vehicle which contains the basic dispersion medium and the required other ingredients from those listed above. Sterile powders for the preparation of sterile injectable solutions can be prepared by vacuum-drying and freeze-drying techniques, which yields a powder of the *Dendrilla membranosa* compounds and/or derivatives thereof with or without any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of the *Dendrilla membranosa* compounds and/or derivatives thereof. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, use of nanotechnology including nanoformulations for parenteral administration can also contain one or more excipients, such as dispersing agents, wetting agents, and suspending agents.

Topical Formulations

The *Dendrilla membranosa* compounds and/or derivatives thereof can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, the *Dendrilla membranosa* compounds and/or derivatives thereof can be administered as a liquid formulation, such as a solution or suspension, a semi-solid formulation, such as a lotion or ointment, or a solid formulation. In some embodiments, the *Dendrilla membranosa* compounds and/or derivatives thereof can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, *ceratonia* extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a non-ionic surfactant. In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing the *Dendrilla membranosa* compounds and/or derivatives thereof are also described herein. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing the *Dendrilla membranosa* compounds and/or derivatives thereof are also described herein. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Ointments containing the *Dendrilla membranosa* compounds and/or derivatives thereof and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing the *Dendrilla membranosa* compounds and/or derivatives thereof, a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include the *Dendrilla membranosa* compounds and/or derivatives thereof. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Enteral Formulations

The *Dendrilla membranosa* compounds and/or derivatives thereof can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing the *Dendrilla membranosa* compounds and/or derivatives thereof can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing the *Dendrilla membranosa* compounds and/or derivatives thereof can be prepared using one or more pharmaceutically acceptable excipients, including diluents, preservatives, binders, lubricants, disintegrators, swelling agents, fillers, stabilizers, and combinations thereof.

Delayed release dosage formulations containing the *Dendrilla membranosa* compounds and/or derivatives thereof can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing the *Dendrilla membranosa* compounds and/or derivatives thereof can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Methods of Using the Compounds and Formulations Thereof

In use, the compounds (including derivatives) and formulations thereof described herein can be administered to a subject. The compounds once administered can antibacterial and/or antibiofilm. The compounds and formulations thereof described herein can be useful for treating and/or preventing a bacterial infection and/or bacterial biofilm in a subject. In some embodiments, the bacterial infection is a Staphylococcus infection. In some embodiments, the Staphylococcus infection is a Staphylococcus aureus infection. The Staphylococcus infection can be a methicillin-resistant Staphylococcus aureus (MRSA) infection. In some embodiments, the bacterial infection is caused by a bacteria is resistant to at least one antibiotic. In some embodiments, the bacterial infection is caused by a bacterial that is resistant to multiple antibiotics.

In some embodiments, an amount of the Dendrilla membranosa compounds and/or derivatives thereof or formulations thereof can be administered to a subject. The subject can have or is suspected of having a bacterial infection and/or bacterial biofilm as described above. The amount administered can be an amount effective to kill a bacterial cell, reduce or inhibit the growth of a bacterial cell. The bacterial cell can be encapsulated in a biofilm. The bacterial cell is not encapsulated in a biofilm.

The Dendrilla membranosa compounds and/or derivatives thereof or formulation thereof described herein can be co-administered or be a co-therapy with another active agent or ingredient that can be included in the formulation or provided in a dosage form separate from the Dendrilla membranosa compounds and/or derivatives thereof or formulation thereof.

The amount of the Dendrilla membranosa compounds and/or derivatives thereof or formulation thereof can range from about 0.1 µg/kg to up to about 1000 mg/kg or more, depending on the factors mentioned elsewhere herein. In certain embodiments, the amount can range from 0.1 µg/kg up to about 500 mg/kg, or 1 µg/kg up to about 500 mg/kg, 5 µg/kg up to about 500 mg/kg, 0.1 µg/kg up to about 100 mg/kg, or 1 µg/kg up to about 100 mg/kg, 5 µg/kg up to about 100 mg/kg.

Administration of the Dendrilla membranosa compounds and/or derivatives thereof or formulation thereof can be systemic or localized. The Dendrilla membranosa compounds and/or derivatives thereof or formulation thereof can be administered to the subject in need thereof one or more times per hour or day. In embodiments, the Dendrilla membranosa compounds and/or derivatives thereof or formulation thereof can be administered once daily. In other embodiments, the Dendrilla membranosa compounds and/ or derivatives thereof or formulation thereof can be administered can be administered 2, 3, 4, 5, 6, 7, 8, 9, 10, 11, 12, or more times daily. In some embodiments, when administered, an effective amount of the s Dendrilla membranosa compounds and/or derivatives thereof or formulation thereof can be administered to the subject in need thereof. The Dendrilla membranosa compounds and/or derivatives thereof or formulation thereof can be administered one or more times per week. In some embodiments, Dendrilla membranosa compounds and/or derivatives thereof or formulation thereof can be administered 1, 2, 3, 4, 5, 6 or 7 days per week. In some embodiments, the Dendrilla membranosa compounds and/or derivatives thereof or formulation thereof can be administered 1, 2, 3, 4, 5, 6, 7, 8, 9, 10, 11, 12, or more times per month. In some embodiments, the Dendrilla membranosa compounds and/or derivatives thereof or formulation thereof can be administered 1, 2, 3, 4, 5, 6, 7, 8, 9, 10, 11, 12, 13, 14, 15, 16, 17, 18, or more time per year.

In some embodiments, the Dendrilla membranosa compounds and/or derivatives thereof or formulation thereof can be administered in a dosage form. The amount or effective amount of the Dendrilla membranosa compounds and/or derivatives thereof or formulation thereof can be divided into multiple dosage forms. For example, the effective amount can be split into two dosage forms and the one dosage forms can be administered, for example, in the morning, and the second dosage form can be administered in the evening. Although the effective amount can be given over two or more doses, in one day, the subject can receives the effective amount when the total amount administered across all the doses is considered. The dosages can range from about 0.1 µg/kg to up to about 1000 mg/kg or more, depending on the factors mentioned above. In certain embodiments, the dosage can range from 0.1 µg/kg up to about 500 mg/kg, or 1 µg/kg up to about 500 mg/kg, 5 µg/kg up to about 500 mg/kg, 0.1 µg/kg up to about 100 mg/kg, or 1 µg/kg up to about 100 mg/kg, 5 µg/kg up to about 100 mg/kg.

Aspects

The following listing of exemplary aspects supports and is supported by the disclosure provided herein.

Aspect 1. A method of treating a biofilm in a subject or preventing the formation of a biofilm produced by bacteria in a subject, the method comprising administering to the subject one or more compounds produced by *Dendrilla membranosa*, one or more derivatives of a compound produced by *Dendrilla membranosa*, or a combination thereof.

Aspect 2. A method of treating or preventing a bacterial infection in a subject, the method comprising administering to the subject one or more compounds produced by *Dendrilla membranosa*, one or more derivatives of a compound produced by *Dendrilla membranosa*, or a combination thereof.

Aspect 3. The method of aspects 1 or 2, wherein the compound or derivative thereof is one or more compounds having the structure I-IV:

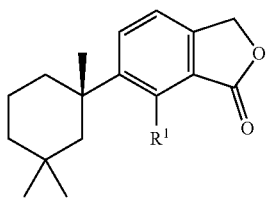

I

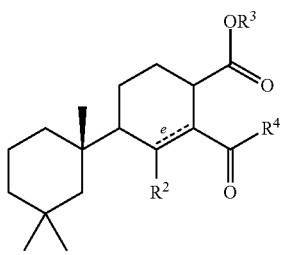

II

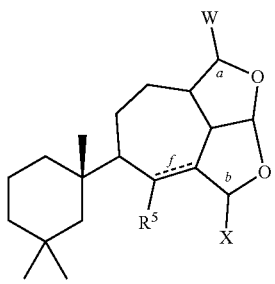

III

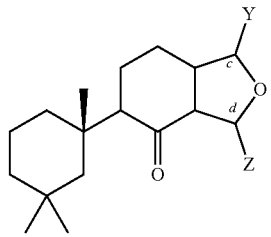

IV wherein $R^4$ to $R^5$ are, independently, hydrogen, an alkyl group, an alkoxy group, an aryl group, or an acyl group;

W, X, Y, and Z are, independently, an oxo group or $OR^6$, where $R^6$ is hydrogen, an alkyl group, an aryl group, or an acyl group; and wherein when W, X, Y, or Z is $OR^6$, the stereochemistry at carbons a, b, c, and d is substantially R, substantially S, or racemic; and bonds e and f are present or not present.

Aspect 4. The method of aspects 1 or 2, wherein the compound or derivative thereof is

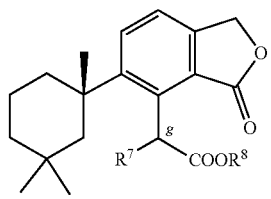

V wherein $R^7$ and $R^8$ are each a $C_1$ to $C_5$ alkyl group, and the stereochemistry at carbon g is substantially R, substantially S, or racemic.

Aspect 5. The method of aspect 4, wherein $R^7$ and $R^8$ are each a methyl group.

Aspect 6. The method of aspect 4, wherein $R^7$ and $R^8$ are each a methyl group, and the stereochemistry at carbon g is substantially R.

Aspect 7. The method of aspects 1 or 2, wherein the compound or derivative thereof is structure II, wherein $R^3$ is a $C_1$ to $C_5$ alkyl group, $R^4$ is hydrogen or a $C_1$ to $C_5$ alkyl group, and bond e is present.

Aspect 8. The method of aspects 1 or 2, wherein the compound or derivative thereof is structure II, wherein $R^2$ is an oxo group, $R^3$ is a $C_1$ to $C_5$ alkyl group, $R^4$ is hydrogen or a $C_1$ to $C_5$ alkyl group, and bond e is present.

Aspect 8. The method of aspects 1 or 2, wherein the compound or derivative thereof is structure VI,

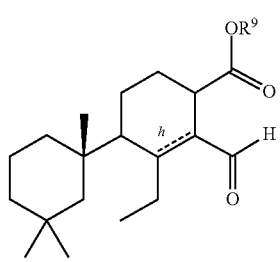

VI wherein $R^9$ is a $C_1$ to $C_5$ alkyl group, and bond h is present or absent.

Aspect 10. The method of aspect 9, wherein $R^9$ is a methyl group.

Aspect 11. The method of aspect 9, wherein $R^9$ is a methyl group and bond h is present.

Aspect 12. The method of aspects 1 or 2, wherein the compound or derivative thereof is structure III, wherein $R^5$ is a $C_1$ to $C_5$ alkyl group, W is an acyl group, X is an oxo group, bond f is present, and the stereochemistry at carbon a is substantially R, substantially S, or racemic.

Aspect 13. The method of aspects 1 or 2, wherein the compound or derivative thereof is structure VII,

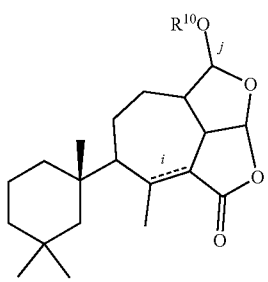

VII wherein $R^{10}$ is $C(O)R^{20}$, wherein $R^{20}$ is a $C_1$ to $C_5$ alkyl group, bond i is present or absent, and the stereochemistry at carbon j is substantially R, substantially S, or racemic.

Aspect 14. The method of aspect 13, wherein $R^{10}$ is C(O)Me and bond i is present.

Aspect 15. The method of aspect 13, wherein $R^{10}$ is C(O)Me, bond i is present, and the stereochemistry at carbon j is substantially S.

Aspect 16. The method of aspects 1 or 2, wherein the compound or derivative thereof is structure IV, wherein Y and Z are each an acyl group, and the stereochemistry at carbons c and d is substantially R, substantially S, or racemic.

Aspect 17. The method of aspects 1 or 2, wherein the compound or derivative thereof is structure VIII,

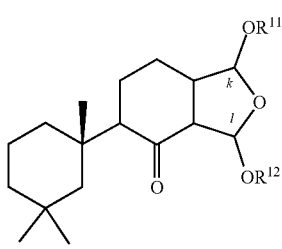

VII wherein $R^{11}$ and $R^{12}$ are each $C(O)R^{20}$, wherein $R^{20}$ is a $C_1$ to $C_5$ alkyl group, and the stereochemistry at carbons k and l is substantially R, substantially S, or racemic.

Aspect 18. The method of aspect 17, wherein $R^{11}$ and $R^{12}$ are each C(O)Me.

Aspect 19. The method of aspect 17, wherein $R^{11}$ and $R^{12}$ are each C(O)Me, the stereochemistry at carbon k is substantially S, and the stereochemistry at carbon I is substantially R.

Aspect 20. The method in any one of aspects 1-19, wherein the compound or derivative thereof is administered to the subject as a unit dose composition comprising a pharmaceutically acceptable carrier.

Aspect 21. The method in any one of aspects 1-20, wherein the compound or derivative thereof is administered to the subject at a dosage of from about 0.1 µg/kg to about 1,000 µg/kg per unit dose composition.

Aspect 22. The method in any one of aspects 1-21, wherein the compound or derivative has $MEBC_{90}$ value less than or equal to 100 µg/mL.

Aspect 23. The method in any one of aspects 1-22, wherein the biofilm is produced by Gram-negative bacteria.

Aspect 24. The method of aspect 23, wherein the Gram-negative bacteria comprises *E. coli, Klebsiella, Enterobacter, H. influenzae, Proteus, Serratia, Pseudomonas* species, or any combination thereof.

Aspect 25. The method in any one of aspects 1-22, wherein the biofilm is produced by Gram-positive bacteria.

Aspect 26. The method of aspect 25, wherein the Gram-positive bacteria comprises methicillin-resistant *Staphylococcus aureus*, a staphylococcal species, or a streptococcal species.

Aspect 27. The method in any one of aspects 1-22, wherein the biofilm is produced by Gram-negative bacteria and Gram-positive bacteria.

Aspect 28. A unit dose composition comprising one or more compounds produced by *Dendrilla membranosa*, one or more derivatives of a compound produced by *Dendrilla membranosa*, or a combination thereof, and a pharmaceutically acceptable carrier.

Aspect 29. The unit dose composition of aspect 28, wherein the composition does not only consist of a single natural product produced by *Dendrilla membranosa*.

Aspect 30. The unit dose composition of aspect 28, wherein the compound or derivative thereof is one or more compounds having the structure I-IV:

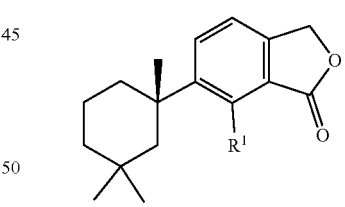

I

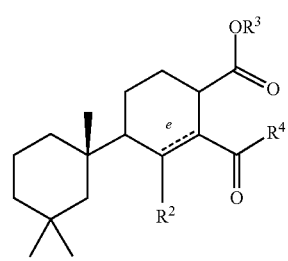

II

III

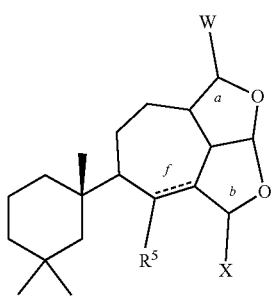

IV

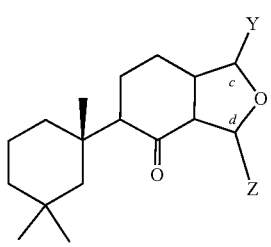

wherein $R^1$ to $R^5$ are, independently, hydrogen, an alkyl group, an alkoxy group, an aryl group, or an acyl group;

W, X, Y, and Z are, independently, an oxo group or $OR^6$, where $R^6$ is hydrogen, an alkyl group, an aryl group, or an acyl group; and wherein when W, X, Y, or Z is $OR^6$, the stereochemistry at carbons a, b, c, and d is substantially R, substantially S, or racemic; and bonds e and f are present or not present.

Aspect 31. The unit dose composition of aspect 28, wherein the compound or derivative thereof is structure VI,

V

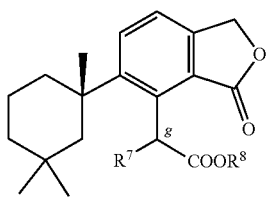

wherein $R^7$ and $R^8$ are each a $C_1$ to $C_5$ alkyl group, and the stereochemistry at carbon g is substantially R, substantially S, or racemic.

Aspect 32. The unit dose composition of aspect 31, wherein $R^7$ and $R^8$ are each a methyl group.

Aspect 33. The unit dose composition of aspect 31, wherein $R^7$ and $R^8$ are each a methyl group, and the stereochemistry at carbon g is substantially R.

Aspect 34. The unit dose composition of aspect 28, wherein the compound or derivative thereof is structure II, wherein $R^3$ is a $C_1$ to $C_5$ alkyl group, $R^4$ is hydrogen or a $C_1$ to $C_5$ alkyl group, and bond e is present.

Aspect 34. The unit dose composition of aspect 28, wherein the compound or derivative thereof is structure II, wherein $R^2$ is an oxo group, $R^3$ is a $C_1$ to $C_5$ alkyl group, $R^4$ is hydrogen or a $C_1$ to $C_5$ alkyl group, and bond e is present.

Aspect 36. The unit dose composition of aspect 28, wherein the compound or derivative thereof is structure VII,

VI

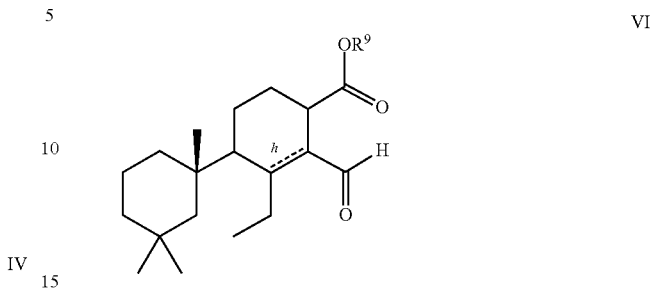

wherein $R^9$ is a $C_1$ to $C_5$ alkyl group, and bond h is present or absent.

Aspect 37. The unit dose composition of aspect 36, wherein $R^9$ is a methyl group.

Aspect 38. The unit dose composition of aspect 36, wherein $R^9$ is a methyl group and bond h is present.

Aspect 39. The unit dose composition of aspect 28, wherein the compound or derivative thereof is structure III, wherein $R^5$ is a $C_1$ to $C_5$ alkyl group, W is an acyl group, X is an oxo group, bond f is present, and the stereochemistry at carbon a is substantially R, substantially S, or racemic.

Aspect 40. The unit dose composition of aspect 28, wherein the compound or derivative thereof is structure VIII,

VII

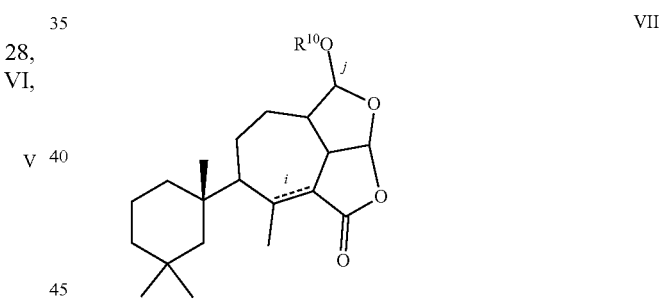

wherein $R^{10}$ is $C(O)R^{20}$, wherein $R^{20}$ is a $C_1$ to $C_5$ alkyl group, bond i is present or absent, and the stereochemistry at carbon j is substantially R, substantially S, or racemic.

Aspect 41. The unit dose composition of aspect 40, wherein $R^{10}$ is C(O)Me and bond i is present.

Aspect 42. The unit dose composition of aspect 40, wherein $R^{10}$ is C(O)Me, bond i is present, and the stereochemistry at carbon j is substantially S.

Aspect 43. The unit dose composition of aspect 28, wherein the compound or derivative thereof is structure IV, wherein Y and Z are each an acyl group, and the stereochemistry at carbons c and d is substantially R, substantially S, or racemic.

Aspect 44. The unit dose composition of aspect 28, wherein the compound or derivative thereof is structure VIII,

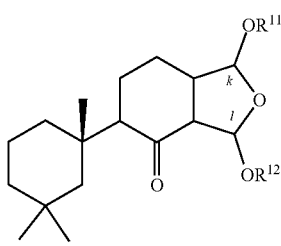

VII wherein $R^{11}$ and $R^{12}$ are each $C(O)R^{20}$, wherein $R^{20}$ is a $C_1$ to $C_5$ alkyl group, and the stereochemistry at carbons k and l is substantially R, substantially S, or racemic.

Aspect 45. The unit dose composition of aspect 44, wherein $R^{11}$ and $R^{12}$ are each C(O)Me.

Aspect 46. The unit dose composition of aspect 44, wherein $R^{11}$ and $R^{12}$ are each C(O)Me, the stereochemistry at carbon k is substantially S, and the stereochemistry at carbon I is substantially R.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Biofilms are formed by all bacterial species, and are a collection of cells coated in an extracellular matrix composed of polysaccharides, proteins, and DNA. In the context of human disease, biofilms are the driving force behind many kinds of chronic infection, including urinary tract infections, upper respiratory infections and periodontitis. Further, biofilms commonly form on implanted medical devices, such as catheters, artificial joints, pacemakers and pins/plates. Estimates suggest that up to 80 percent of all infections are believed to be caused by bacterial biofilms, making them a serious public health concern. This problem is compounded by the observation that bacterial cells within a biofilm are protected from exposure to factors of the innate immune system, making them difficult to eradicate. This is exacerbated by the observation that bacterial cells within a biofilm are also innately resistant to therapeutic intervention. This is thought to be caused by antibiotic penetration and stability is significantly impaired by the biofilm matrix. Additionally, many cells within a biofilm are essentially dormant, leading to what is known as a persister phenotype. Such metabolically inactive persister cells are entirely unaffected by therapeutics, which largely target actively growing cells. Thus, upon cessation of chemotherapeutics, persister cells flourish, repopulating an infections niche, and restarting an active infection. Intervention strategies targeting multidrug resistant organism (MDRO) biofilms would save numerous lives and significantly limit morbidity. However, present options for controlling and eradicating biofilms during infection are almost non-existent. For implant driven infections, the best course of action is typically to remove the infected object. However, in the case of prostheses and cardiac implants, such a course of action is not always an option. As such, there is an urgent and desperate need to develop molecules that can actively impact cell viability within biofilms.

This Example describes and can demonstrate compounds that can be antibacterial and can kill or inhibit cells within a biofilm.

Darwinolide (24) was isolated from the sponge *Dendrilla membranosa*. Darwinolide bears a seven-membered central ring, which differs from other spongian diterpenes that had previously been described from sponges from the same geographical region. Studies spanning over two decades into this sponge had never before revealed such a compound, thus this discovery can demonstrate the plasticity of this sponge in response to spatial and/or temporal factors or stimuli. Darwinolide was observed to have a MIC of about 132.9 µM in a standard MRSA assay. Darwinolide was observed to have a MIC of 33.2 µM in a standard biofilm assay, which was twofold less than the mammalian (J773) toxicity of 73.4 µM, when tested using a mammalian cytotoxicity assay.

The following natural and semisynthetic compounds had MRSA biofilm bioactivity:

Membranolide (3): MBEC90<25 mg/mL
ABO-1 (17): MBEC90 50 mg/mL
Darwinolide (24): MBEC90 35 mg/mL
Keto-DHG (19): MBEC90 50 mg/mL.

Figure 2:
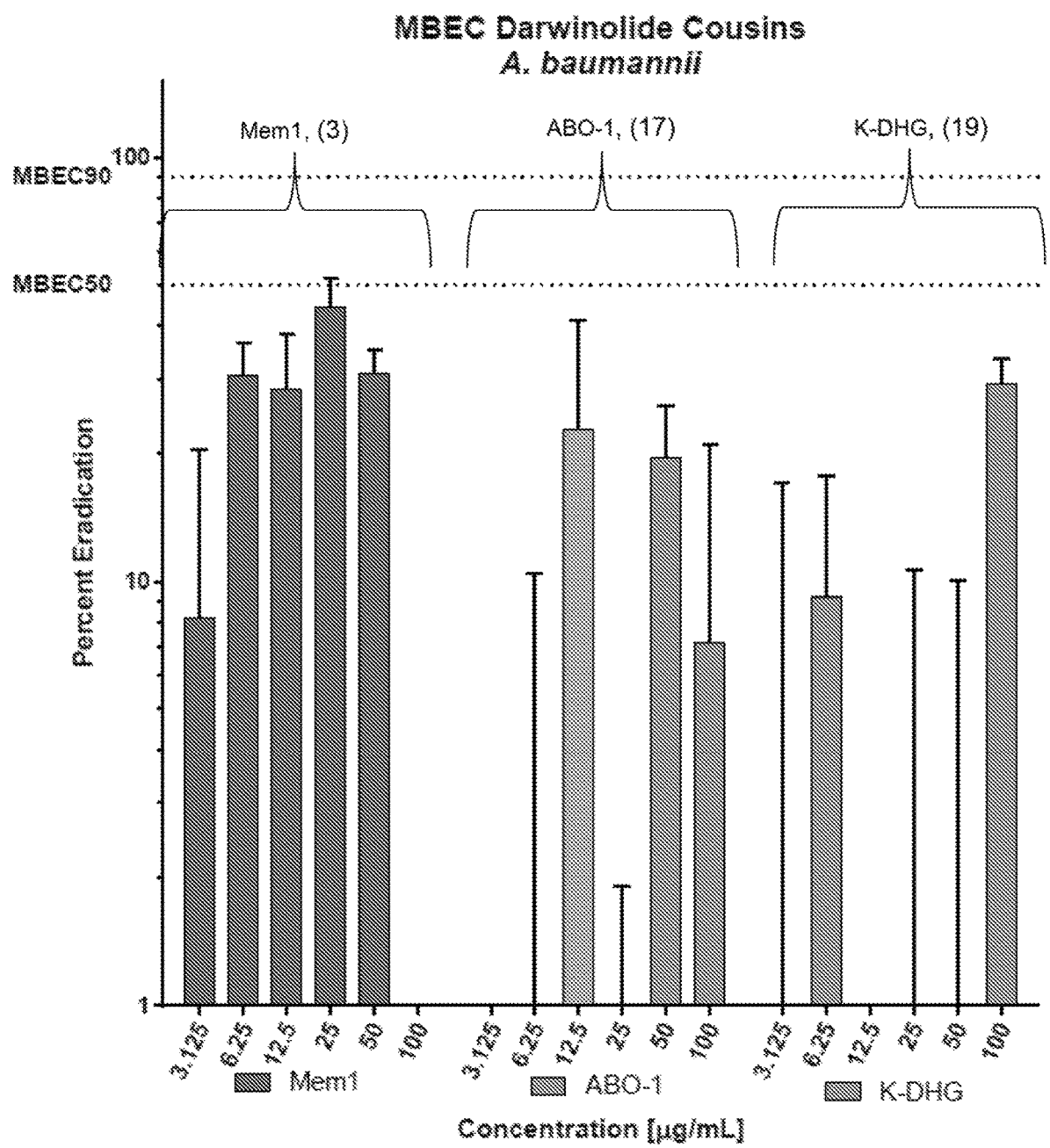
FIG. 2 shows a graph that can demonstrate the minimum biofilm eradication concentration (MBEC) of three lead compounds against multi-drug resistant *A. baumannii* at varying concentrations represented as percent eradication. Each sample was tested in triplicate for all concentrations. Calculated based on no drug controls and represented as a log 10 scale. Error=±SEM. MBEC 90/50: level to which 90% or 50% of the population was eradicated compared to no treatment.

Compounds 7, 8, 18, and 20 lacked MRSA biofilm bioactivity. The MBEC values for several compounds is shown in FIGS. 1 and 2.

Example 2

A Synthetic Scheme for Production of *Dendrilla membranosa* sesquiterpenes.

Darwinolide (24) is a member of a family of related sesquiterpenes that have been isolated from the Antarctic sponge *Dendrilla membranosa*. These secondary metabolites, including tetrahydroapylsulphurin (2) (THAS), aplysulphurin (1) (AS), and membranolide (3) (Mem-1) are in limited supply from natural sources there is a need for the development of synthetic approaches to producing these compounds. This Example describes, inter alia, a synthesis scheme for the production of these and analogue compounds.

Scheme 9 shows a synthesis scheme for the production of darwinolide and related compounds.

Scheme 9

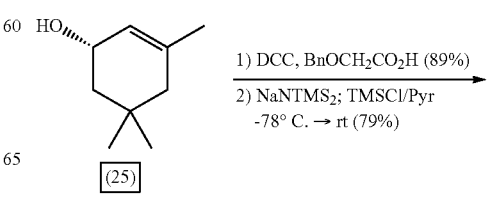

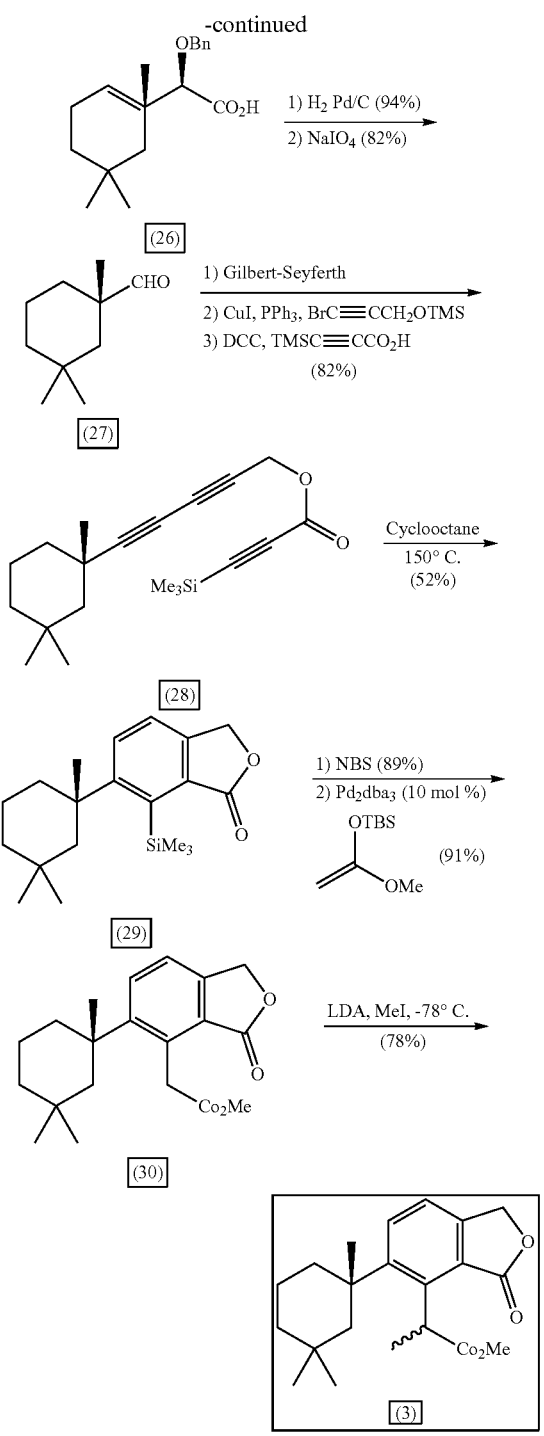

of the additional alpha-sterocenter formed at this step. While this is not important for the synthesis of the membranolide, it is important for the synthesis of the darwinolide.

Hydrogenation of the resulting cyclohexene of (26) with concomitant debenzylation of the ether sets the stage for a periodate cleavage, which provides a quaternary aldehyde (27). Conversion of this aldehyde into the corresponding acetylene was achieved using the Gilbert-Seyferth reaction, which could be smoothly elaborated to the corresponding diyne and acylated with silylated propiolic acid to give triyne (28) in a good yield over 3 steps. These steps can be conducted as a single operation to minimize issues with the volatility of the intermediates. From (28), a hexadehydro-Diels Alder (HDDA) cyclization reaction can yield (29) (the membranolide skeleton) as the major product. (29) can be bromodesilylated and Heck coupling can yield des-methyl membranolide A (30). Methylation of (30) can yield (1) as well as its epimer.

Example 3

Extraction and Isolation of *D. Membranosa* Compounds.
General Procedures

All solvents were obtained from Fisher Scientific Co. and were HPLC grade (>99% purity) unless otherwise stated. All MPLC fractionation were performed on Teledyne-ISCO MPLC with UV-Vis detection. All HPLC fractionation were performed either on an Agilent preparative 1200 LC system equipped with a photodiode array detector (DAD) and a fraction collector or a Shimadzu LC20-AT system equipped with DAD (M20A) and ELSD detectors using Phenomenex Luna C18 or Silica semi-preparative (250×10 mm, 5 μm) or analytical (250×4.6 mm, 5 μm) conditions.

Analytical LCMS was performed on a Phenomenex Kinetex C18 column (50×2.1 mm, 2.6 μm) with an Agilent 6540 LC/QToF-MS equipped with electrospray ionization detection. Optical rotations were measured on a polarimeter. All NMR spectra were acquired in $CDCl_3$ with residual solvent referenced as an internal standard (7.26 ppm). $^1$H-NMR were recorded either on an Inova 400 MHz, a Varian 500 MHz direct-drive instrument equipped with cold-probe detection or an Inova 600 MHz. $^{13}$C-NMR spectra were recorded at the corresponding frequency on the same instruments respectively.

Collection of *Dendrilla membranosa*

Sponge samples were collected using scuba from various sites around Palmer Station, Antarctica in the austral summers of 2016 and 2017. The collection sites chosen were Norsel Point (64°45.674'S, 64°05.467'W), Bonaparte Point (64°46.748'S, 64°02.542'W), Gamage Point (64°46.345'S 64°02.915'W), and Laggard Island (64°48.568'S, 64 00.984'W) at depths between 5-35 m below sea level. Samples were lyophilized and transported back to the University of South Florida where tissues were extracted. Two collections of *Dendrilla membranosa* collected in 2016 and 2017 were obtained and called PSC16-30 and PSC17-16 respectively. The PSC code stands for Palmer Station Collection following by the date and a collection trip number.

Extraction Procedures
PSC16-30:

Samples from Antarctica, (approx. 1 kg of freeze-dried *D. membranosa*) were blended with a Waring CB15N Blender. The resulting powder was poor in a flask and submerged by DCM for 24 h. The mixture was then filtered and the procedure was repeated twice. The three methylene chloride extracts were combined and dried under vacuo. The lipophilic extract (35.2 g) was absorbed onto C18 silical gel (150

Scheme 9 begins from the known optically-pure isophorol (25), which can be obtained in 99% ee via enzymatic acetylatin of the readily available racemate with vinyl acetate and inexpensive *Candida rugosa* lipase. Esterification of the allylic alcohol with benzylated glycolic acid sets the stage for an Ireland Claisen rearrangement that installs the quaternary center needed for the entire Darwinolide family as well as a variety of other products including gracilin A and its various congeners, apysilla A and B, dendrillin, splendidalactone 1, the cadlinolides, and the oxeatamides. Additionally, carboxylate (26) is a crystalline intermediate, which allows for x-ray data to show the control g) and put in 2 MPLC 65 g cartridges. C18 Column Reveleris Grace 40 µm 220 g was used as a plug and flush with acetonitrile at 125 ml/min for 15 minutes. The purification was performed by 2 MPLC runs. The resulting fractions were analyzed by NMR and the first fraction (so-called A) of each run were combined and dried under vacuo. 4.5 g of dried eluate were obtained, loaded on SiO$_2$ (18 g) and separated by MPLC in normal phase gradient (hexane:EtOAc, (0:1-+1:0, v/v)). Further purifications were needed and crystallization as well as preparative, semi-preparative or analytical HPLC were performed to obtained pure compounds.

PSC17-16:

Samples from Antarctica, (3.34 kg of freeze-dried *D. membranosa*) were blended with a Waring CB15N Blender. The resulting powder was poor in a flask and submerged by DCM for 24 h. The mixture was then filtered and the procedure was repeated twice. The three methylene chloride extracts were combined and dried under vacuo. The lipophilic extract (168.1 g) was absorbed onto C18 silical gel (150 g) and put in 6 MPLC cartridges. C18 Column Reveleris Grace 40 µm 220 g was used as a plug and flush with acetonitrile at 125 ml/min for 15 minutes. The purification was performed by 6 MPLC runs. The resulting fractions were analyzed by NMR and the first fraction (So-called A) of each runs were combined and dried under vacuo. 19.221 g of dried eluate were obtained, loaded on SiO$_2$ (48 g) and separated by MPLC in normal phase gradient (hexane:EtOAc, (0:1-1:0, v/v)). The individual fractions were purified by either NP HPLC (normal phase high performance liquid chromatography) using hexanes/ethyl acetate or reversed phase (RP) HPLC using acetonitrile/water to give compounds 1-3, 5, 10, 13-16, and 18-21, as well as the unknown norditerpenes 17.

Pure Compounds Obtained:

Scheme 1: Gracilan derivatives

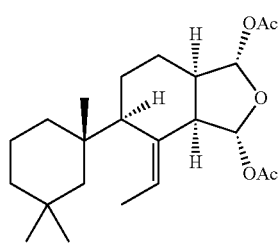

(13)

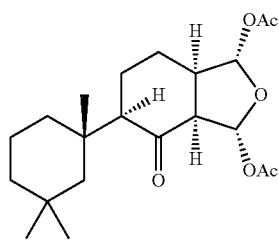

(19)

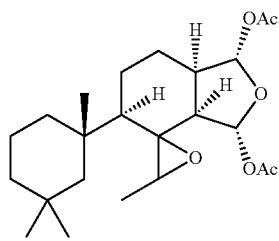

(21)

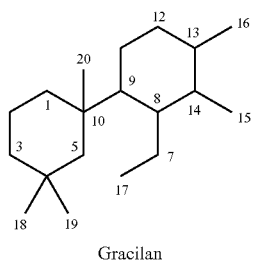

Gracilan 9,11 Dihydrogracilin A (13) was obtained as a clear oil. HRESIMS m/z 415.245 [M+Na]$^+$ 417.246 calculated for C$_{23}$H$_{36}$O$_5$Na. $^1$H-NMR and $^{13}$C NMR data see Table 1. Chemicals shifts were already reported in litterature[1].

TABLE 1

| NMR Data$^a$ of 9, 11-Dihydrogracillin A (13) | | |
|---|---|---|
| | $\delta_C{}^b$ | $\delta_H{}^c$ |
| 1 | 36.5 | 1.55-1.14 (2H, m, ov) |
| 2 | 19.3 | 1.55-1.14 (2H, m, ov) |
| 3 | 39.0 | 1.55-1.14 (2H, m, ov) |
| 4 | 31.1 | — |
| 5 | 50.3 | 1.55-1.14 (2H, m, ov) |
| 7 | 130.1 | 5.65 (1H, q, 6.9) |
| 8 | 134.0 | — |
| 9 | 46.6 | 2.42 (1H, dd, 4.2, 6.8) |
| 10 | 39.0 | — |
| 11α | 23.1 | 1.55-1.14 (1H, m, ov) |
| β | | 1.84 (1H, m) |
| 12 | 23.0 | 1.55-1.14 (2H, m, ov) |
| 13 | 46.0 | 2.35 (1H, ddd, 8.6, 7.7, 7.5) |
| 14 | 27.5 | 3.15 (1H, dd, 7.7, 5.5) |
| 15 | 100.8 | 6.45 (1H, d, 5.5) |
| 16 | 103.1 | 5.97 (1H, s) |
| 17 | 15.7 | 1.65 (3H, d, 6.9) |
| 18 | 27.5 | 0.97 (3H, s) |
| 19 | 35.9 | 0.89 (3H, s) |
| 20 | 24.0 | 1.03 (3H, s) |
| OAc | 170.0 $^{not\ detected}$ | — |
| CH$_3$ | 21.3 | 2.07 & 2.10 (3H, S) |

$^a$in CDCl$_3$, $^b$101 MHz; $^c$400 MHz, ppm [integ., mult., J (Hz)]; ov—overlapping signals; m—complex multiplet.

1) Ozonolysis of 9,11-Dihydrogracilin A:

Scheme 2: Ozonolysis of 9, 11-dihydrogracilin A

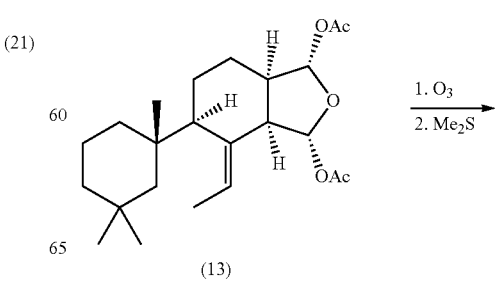

(13)

-continued

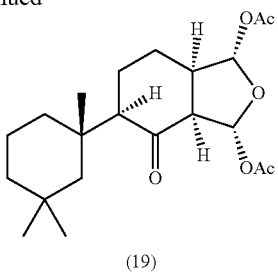

(19)

9,11-Dihydrogracillin A (13) (9 mg) was dissolved in 2000 μl of Hexanes and ozone was bubbled through the solution kept at 0° C. The reaction was incubated for 5 min, after which 500 μl of dimethyl sulfide were added and incubated for 45 min at 0° C.[2]. Solvent was removed with nitrogen gas and residues were resuspended in 300 μl of DCM. NP-HPLC was used to purified the extract and 3.5 mg (39%) of derivative (19) was obtained. HRESIMS m/z 403.209 [M+Na]$^+$ 403.209 calculated for $C_{21}H_{32}O_6Na$. $^1$H-NMR and $^{13}$C NMR data see Table 2. $^1$H-NMR (400 MHz, CDCl$_3$): signals at 1.16 (2H, m), 1.29 (2H, m, ov) 1.43 (1H, m), 1.53 (1H, m), 1.63 (1H, m), 1.78 (1H, m), 1.96 (1H, m), 2.24 (1H, dd, 11.8, 5.6) could not be attributed to a specific carbon but they belong to carbons number 1-3, 11&12.

Scheme 3: Conversion of 9, 11-dihydrogracilin A (13) to dendrillin (21)

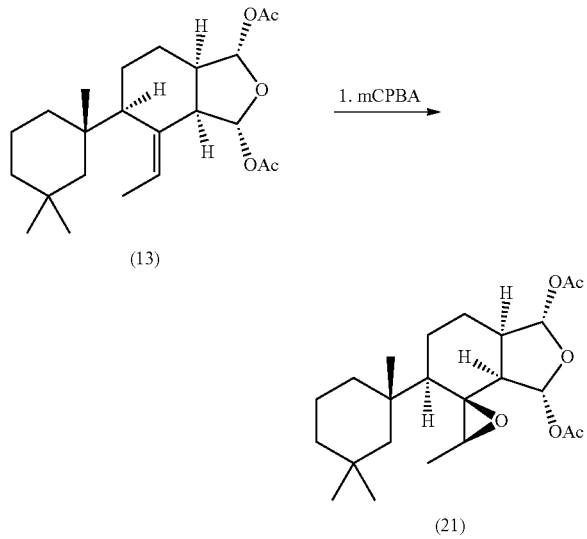

2) Conversion of 9,11-Dihydrogracilin a (13) to Dendrillin (21)

TABLE 2

NMR Data$^a$ of a keto derivative of 9, 11-Dihydrogracillin A (19)

| | $\delta_H{}^c$ |
|---|---|
| 5 | 1.30 (2H, ov d, 13.6) |
| 9 | 2.13 (1H, ov m,) |
| 13 | 3.02 (1H, m) |
| 14 | 3.06 (1H, m) |
| 15 | 6.05 (1H, d, 4.4) |
| 16 | 6.72 (1H, s) |

TABLE 2-continued

NMR Data$^a$ of a keto derivative of 9, 11-Dihydrogracillin A (19)

| | $\delta_H{}^c$ |
|---|---|
| 18 | 0.95 (3H, s) |
| 19 | 0.84 (3H, s) |
| 20 | 1.06 (3H, s) |
| CH$_3$COO | 2.06 & 2.09 (3H, S) |

$^a$in CDCl$_3$, $^c$400 MHz, ppm [integ., mult., J (Hz)]; ov—overlapping signals; m—complex multiplet.

To a solution of 47.2 mg 9,11-dihydrogracillin A (13) (0.12 mmol) in 10 ml of CH$_2$Cl$_2$ was added 24.2 mg of m-CPBA (0.14 mmol). After reflux overnight, the reaction was quenched with 20 mL of 10% NaOH (aq) and the aqueous layer re-extracted with CH$_2$Cl$_2$. Combined organic layers were purified by NP-HPLC (hexane to EtOAc) to yield 13 mg (0.03 mmol, 25%) of (21). Also known as a natural product, dendrillin[3]. HRESIMS m/z 431.241 [M+Na]$^+$ 431.240 calculated for $C_{23}H_{36}O_6Na$. $^1$H-NMR and $^{13}$C NMR data see Table 3.

TABLE 3

NMR Data of dendrillin (21)

| | $\delta_C{}^b$ | $\delta_H{}^c$ |
|---|---|---|
| 1α | 36.0 | 1.62-1.49 (1H, ov m) |
| β | | 1.42-1.31 (1H, ov m) |
| 2 | 19.1 | 1.62-1.49 (2H, ov m) |
| 3α | 38.7 | 1.42-1.31 (1H, ov m) |
| β | | 1.06-1.03 (1H, ov m) |
| 4 | 31.2 | — |
| 5α | 51.6 | 1.42-1.31 (1H, ov m) |
| β | | 1.06-1.03 (1H, ov m) |
| 7 | 62.8 | 3.02 (1H, q, 5.7) |
| 8 | 61.7 | — |
| 9 | 47.9 | 1.42-1.31 (1H, ov m) |
| 10 | 37.5 | — |
| 11α | 21.8 | 1.80-1.70 (1H, ov m) |
| β | | 1.62-1.49 (1H, ov m) |
| 12α | 22.3 | 1.92 (1H, br d, ≈14) |
| β | | 1.80-1.70 (1H, ov m) |
| 13 | 43.8 | 2.61 (1H, m) |
| 14 | 51.6 | 2.04 (1H, ov m) |
| 15 | 97.9 | 6.57 (1H, d, 6.5) |
| 16 | 101.8 | 5.93 (1H, s) |
| 17 | 16.0 | 1.38 (3H, d, 5.7) |
| 18 | 27.5 | 0.96 (3H, s) |
| 19 | 35.7 | 0.86 (3H, s) |
| 20 | 24.0 | 1.12 (3H, s) |
| CH$_3$COO | 170.0 & 169.9 | — |
| CH$_3$COO | 21.2 & 21.2 | 2.10 & 2.05 (3H, s) |

$^a$in CDCl$_3$, $^b$101 MHz; $^c$400 MHz, ppm [integ., mult., J (Hz)]; ov—overlapping signals; m—complex multiplet.

Scheme 4: Aplysulfuran derivatives, aplysulphurin (1), tetrahydroaplysulfurin (2), cadlinolide C (14), membranoid A (5) and G (10), membranolide (3)

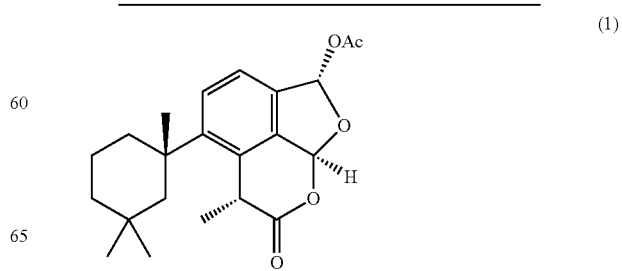

(1)

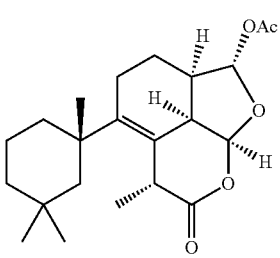

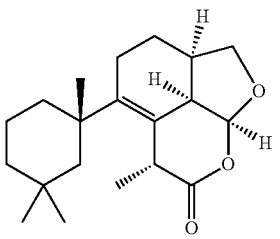

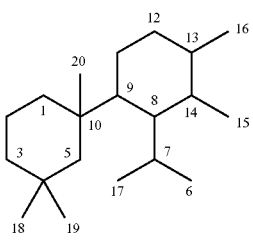

(Aplysulfuran)

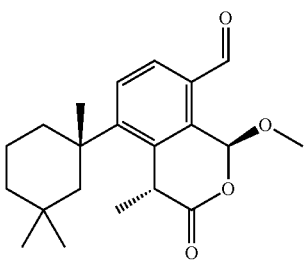

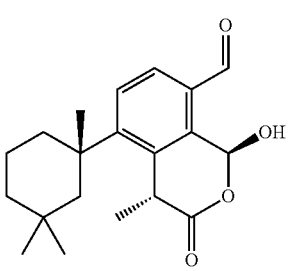

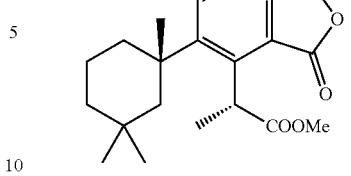

Aplysulphurin (1) was obtained as the major component of a MPLC fraction. Crystallization from hexane gave white crystals that were analyzed by X-Ray as well as HRESIMS m/z 395.183 [M+Na]$^+$ 395.183 calculated for $C_{22}H_{28}O_5Na$. $^1$H-NMR and $^{13}$C NMR datas see Table 4. The structure is known and already published in litterature[4, 5]

TABLE 4

NMR Data of aplysulphurin (1)

| | $\delta_C{}^b$ | $\delta_H{}^c$ |
|---|---|---|
| 1α | 38.6 | 1.46 (1H, ov m) |
| β | | 2.26 (1H, br d, 13.6) |
| 2α | 19.1 | 1.72-1.60 (2H, ov m) |
| 3 | 39.4 | 1.33-1.22 (2H, ov m) |
| 4 | 31.7 | |
| 5α | 50.8 | 1.53 (1H, d, 14.0) |
| β | | 1.96 (1H, br d, 14.0) |
| 6 | 170.7 | |
| 7 | 41.6 | 4.40 (1H, q, 7.4) |
| 8 | 131.9 | |
| 9 | 148.7 | |
| 10 | 38.9 | |
| 11 | 129.2 | 7.51 (1H, d, 8.2) |
| 12 | 122.3 | 7.35 (1H, d, 8.2) |
| 13 | 133.3 | |
| 14 | 137.8 | |
| 15 | 100.3 | 7.07 (1H, d, 1.8) |
| 16 | 101.9 | 7.27 (1H, d, 1.8) |
| 17 | 17.3 | 1.74 (3H, d, 7.4) |
| 18 | 27.5 | 1.23 (3H, s) |
| 19 | 32.5 | 0.96 (3H, s) |
| 20 | 32.7 | 0.52 (3H, s) |
| CH$_3$COO | 169.6 | — |
| CH$_3$COO | 20.8 | 2.16 (3H, s) |

$^a$in CDCl$_3$, $^b$101 MHz; $^c$400 MHz, ppm [integ., mult., J (Hz)]; ov—overlapping signals; m—complex multiplet.

Tetrahydroaplysulfurin (2) was obtained as a clear oil. HRESIMS m/z 399.213 [M+Na]$^+$, 399.214 calculated for $C_{22}H_{32}O_5Na$. $^1$H-NMR and $^{13}$C NMR data see Table 5. The structure is known and already published in literature[6, 7]

TABLE 5

NMR Data of tetrahydroaplysulphurin (2)

| | $\delta_C{}^b$ | $\delta_H{}^c$ | COSY | HMBC |
|---|---|---|---|---|
| 1α | 38.8 | 1.51 (1H, ov m) | | |
| β | | 2.10 (1H, ov m) | | |
| 2α | 25.0 | 2.33 (1H, br ddd, 17.4, 5.5, 4.8) | H-2β, H-1β, H-3 | |
| β | | 1.88 (1H, ov dd) | | |
| 3α | 39.4 | 1.26 (1H, ov m) | | |
| β | | 1.06 (1H, ovm) | | |
| 4 | 31.5 | | | |

TABLE 5-continued

NMR Data of tetrahydroaplysulphurin (2)

| | $\delta_C{}^b$ | $\delta_H{}^c$ | COSY | HMBC |
|---|---|---|---|---|
| 5α | 50.8 | 1.25 (1H, ov d, 13.8) | H-5β | |
| β | | 1.76 (1H, br d, 13.8) | H-5α | |
| 6 | 169.8 | | | |
| 7 | 40.7 | 4.19 (1H, q, 7.4) | | 17, 14, 8, 9, 6 |
| 8 | 121.3 | | | |
| 9 | 146.4 | | | |
| 10 | 39.5 | | | |
| 11 | 20.7 | 1.50 (2H, m) | | |
| 12α | 23.9 | 1.89 (1H, ov m) | | |
| β | | 1.28 (1H, ov m)) | | |
| 13 | 42.6 | 2.51 (1H, dddd, , 6.3, 2.3 | H-16, H14, H-12 α β | |
| 14 | 38.0 | 3.21 (1H, br dd, 6.3) | | |
| 15 | 102.7 | 5.98 (1H, d, 6.3) | | 14 |
| 16 | 100.5 | 6.15 (1H, d, 2.3) | | 14, 15, 12, 8 |
| 17 | 14.7 | 1.41 (3H, d, 7.4) | | |
| 18 | 28.3 | 0.75 (3H, s) | | |
| 19 | 32.4 | 0.88 (3H, s) | | |
| 20 | 31.0 | 1.10 (3H, s) | | |
| CH₃COO | 21.1 | 2.06 (3H, s) | | |
| CH₃COO | 170.9 | | | |

[a]in CDCl₃; [b]100 MHz; [c]400 MHz, ppm [integ., mult., J (Hz)]; ov—overlapping signals; m—complex multiplet.

Cadlinolide C (14) was obtained as a clear oil. HRESIMS m/z 319.226 [M+H]⁺ 319.227 calculated for $C_{20}H_{31}O_3$. ¹H-NMR and ¹³C NMR data see Table 6. The structure is known and already published in literature[8]

TABLE 6

NMR Data of cadlinolide C (14)

| | $\delta_H{}^c$ |
|---|---|
| 1α | 1.10 (1H, ov m) |
| β | 1.92 (1H, ov m) |
| 2 | 1.50 (2H, ov m) |
| 3α | 1.20 (1H, m) |
| β | 1.31 (1H, m) |
| 5α | 1.26 (1H, d, 13.7) |
| β | 1.80 (1H, dt, 13.7, 1.7) |
| 7 | 4.17 (1H, ov m) |
| 11α | 1.92 (1H, ov m) |
| β | 2.48 (1H, m) |
| 12α | 0.90 (1H, ov m) |
| β | 1.92 (1H, ov m) |
| 13 | 2.64 (1H, m) |
| 14 | 3.02 (1H, ddd, 12.0, 5.7, 2.2) |
| 15 | 6.02 (1H, d, 5.7) |
| 16α | 3.59 (1H, dd, 9.9, 8.8) |
| β | 4.17 (1H, ov m) |
| 17 | 1.40 (3H, d, 7.4) |
| 18 | 0.76 (3H, s) |
| 19 | 0.90 (3H, s) |
| 20 | 1.14 (3H, s) |

[a]in CDCl₃; [c]400 MHz, ppm [integ., mult., J (Hz)]; ov—overlapping signals; m—complex multiplet.

Membranoid A (5) was obtained as a clear oil. HRESIMS m/z 345.206 [M+H]⁺ 345.206 calculated for $C_{21}H_{39}O_4$. ¹H-NMR and ¹³C NMR data see Table 7. Stereochemistry was attributed by comparison with the literature[9] especially the H15 chemical shift.

TABLE 7

NMR Data of membranoid A (5)

| | $\delta_H{}^c$ |
|---|---|
| 1α | 1.50 (1H, ov m) |
| β | 2.23 (1H, br d, 14.3) |
| 2 | 1.73 (2H, m) |
| 3 | 1.34 (2H, ov m) |
| 5α | 1.59 (1H, d, 14.5) |
| β | 2.06 (1H, d, 14.5) |
| 7 | 4.54 (1H, q, 7.2) |
| 11 | 7.76 (1H, d, 8.3) |
| 12 | 7.72 (1H, d, 8.3) |
| 15 | 6.83 (1H, s) |
| 16 | 10.06 (1H, s) |
| 17 | 1.82 (3H, d, 7.2) |
| 18 | 0.58 (3H, s) |
| 19 | 0.98 (3H, s) |
| 20 | 1.32 (3H, s) |
| 21 (OMe) | 3.82 (3H, s) |

[a]in CDCl₃; [c]400 MHz, ppm [integ., mult., J (Hz)]; ov—overlapping signals; m—complex multiplet.

Membranoid G (10) was obtained as a clear oil. HRESIMS m/z 331.190 [M+H]⁺ 331.190 calculated for $C_{20}H_{27}O_4$. ¹H-NMR and ¹³C NMR data see Table 8. Published as a semisynthetic derivative from aplysulphurin by P. Karuso[5]

TABLE 8

NMR Data of Membranoid G (10)

| | $\delta_H{}^c$ |
|---|---|
| 1α | 1.53 (1H, ov m) |
| β | 2.24 (1H, bdt) |
| 2α | 1.75 (1H, ov m) |
| β | 1.81 (1H, ov m) |
| 3 | 1.35 (2H, ov m) |
| 5α | 1.61 (1H, d, 14.1) |
| β | 2.06 (1H, bd 14.1) |
| 7 | 4.57 (1H, q, 7.2) |
| 11 | 7.77 (1H, d, 8.3) |
| 12 | 7.73 (1H, d, 8.3) |
| 15 | 7.23 (1H, bs, 1.5) |
| 16 | 6.30 (1H, d, 1.6) |
| 17 | 1.67 (3H, s) |
| 18 | 0.47 (3H, s) |

TABLE 8-continued

| | NMR Data of Membranoid G (10) | |
|---|---|---|
| | | $\delta_H{}^c$ |
| 19 | | 0.92 (3H, s) |
| 20 | | 1.38 (3H, s) |

$^a$ in CDCl$_3$, $^c$400 MHz, ppm [integ., mult., J (Hz)]; ov—overlapping signals; m—complex multiplet.

Membranolide (3) was obtained as a clear oil. HRESIMS m/z 345.207 [M+H]$^+$ 345.206 calculated for C$_{21}$H$_{32}$O$_4$. $^1$H-NMR and $^{13}$C NMR data see Table 9.

TABLE 9

| | NMR Data of Membranoilide (3) | | |
|---|---|---|---|
| | $\delta_C{}^b$ | $\delta_H{}^c$ | HMBC |
| 1α | 40.9 | 1.49 (1H, ov m) | |
| β | | 2.28 (1H, br dt, 14.2, 2.5) | |
| 2α | 20.0 | 1.70 (1H, ov m) | |
| β | | 1.82 (1H, ov m) | |
| 3 | 39.4 | 1.28 (2H, ov m) | |
| 4 | 31.7 | | |
| 5α | 50.9 | 1.53 (1H, d, 14.0) | |
| β | | 2.08 (1H, br d, 14.0) | |
| 6 | 173.7 | | |
| 7 | 40.5 | 4.61 (1H, q, 7.1) | 17, 14, 8, 6 |
| 8 | 141.8 | | |
| 9 | 148.0 | | |
| 10 | 39.3 | | |
| 11 | 132.9 | 7.81 (1H, d, 8.3) | 8, 9 |
| 12 | 120.2 | 7.31 (1H, dt, 8.3, 0.8) | 9, 14 |
| 13 | 145.9 | | |
| 14 | 124.6 | | |
| 15 | 170.7 | | |
| 16 | 68.3 | 5.21 (2H, br s) | 12, 13, 14, 15 |
| 17 | 17.7 | 1.67 (3H, s) | 6, 7, OCH$_3$ |
| 18 | 27.4 | 0.47 (3H, s) | 3, 4, 5, 19 |
| 19 | 32.7 | 0.93 (3H, s) | 3, 4, 5, 18 |
| 20 | 22.7 | 1.38 (3H, s) | 1, 5, 9, 10 |
| OCH$_3$ | 52.0 | 3.67 (3H, s) | |

$^a$ in CDCl$_3$, $^b$100 MHz; $^c$400 MHz, ppm [integ., mult., J (Hz)]; ov—overlapping signals; m—complex multiplet.

3) Ozonolysis of THAS:

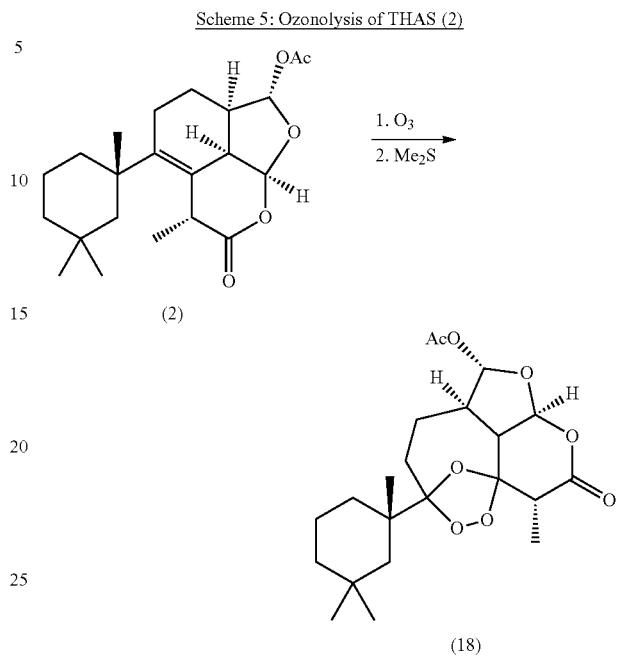

Scheme 5: Ozonolysis of THAS (2)

To produce the di-keto derivative of THAS (5) we isolated the intermediate (10) Ozone, which was generated by O$_2$ flowing at 0.5 ml/min through a Telsa coil, was bubbled through a solution of THAS (2) (15 mg) in 2500 μl of DCM kept at 0° C. The reaction was incubated for 5 min, after which 500 μl of dimethyl sulfide were added and incubated for 45 min at 0° C. Solvent was eliminated under nitrogen gas and residues were dissolved in 300 μl of DCM and NP-HPLC used to isolate products. 3.8 mg of trioxolane product (18) corresponding to 22.5% yield, were isolated and used for the spectroscopic characterization. HRESIMS m/z 447.199 [M+Na]$^+$ 447.199 calculated for C$_{22}$H$_{32}$O$_8$Na. $^1$H-NMR and $^{13}$C NMR data see Table 10.

TABLE 10

| | NMR Data of trioxolane product (18) | | | |
|---|---|---|---|---|
| | $\delta_C{}^b$ (HSQC) | $\delta_H{}^c$ | COSY | HMBC |
| 1α | 30.5 (CH$_2$) | 1.23 (1H, m) | | |
| β | | 1.40 (1H, m) | | |
| 2 | 18.3 (CH$_2$) | 1.47 (2H, m) | H-2β, H-1 α, β, H-3 | |
| 3α | 38.7 (CH$_2$) | 1.01-1.05 (1H, m) | | |
| β | | 1.33 (1H, ov m) | | |
| 4 | 30.6 (C$_{quat}$) | — | | |
| 5α | 43.5 (CH$_2$) | 1.12 (1H, br d, 13.6) | H-5 β | |
| β | | 1.32 (1H, ov m) | H-5 α | |
| 6 | 168.5 (C$_{quat}$) | | | |
| 7 | 42.8 (CH) | 3.01 (1H, q, 7.8) | H$_3$-17 | 17, 14, 8, 6 |
| 8 | 108.5 (C$_{quat}$) | | | |
| 9 | 117.2 (C$_{quat}$) | | | |
| 10 | 41.4 (C$_{quat}$) | | | |
| 11α | 28.7 (CH$_2$) | 2.23 (1H, m) | H-11β, H-12 | |
| β | | 1.75 (1H, m) | H-11α, H-12 | |
| 12 | 22.6 (CH$_2$) | 1.91-2.01 (2H, m) | | |
| 13 | 45.5 (CH) | 2.62 (1H, m) | H-12, H-16, H14 | |
| 14 | 43.0 (CH) | 3.08 (1H, dd, 7.0, 8.0) | H-15, H-13 | 12, 13, 15, 8 |
| 15 | 101.9 (CH) | 6.06 (1H, d, 6.6) | H-14 | 14, 13, 8, 6 |
| 16 | 101.8 (CH) | 6.29 (1H, d, 2.2) | H-13 | 12, 14, 13, 15, OAc |
| 17 | 11.9 (CH$_3$) | 1.34 (3H, d, 7.8) | | 6 |
| 18 | 27.5 (CH$_3$) | 0.94 (3H, s) | | 3, 4, 5, 19 |

TABLE 10-continued

NMR Data of trioxolane product (18)

| $\delta_C^b$ (HSQC) | $\delta_H^c$ | COSY | HMBC |
|---|---|---|---|
| 19 | 35.5 ($CH_3$) | 0.87 (3H, s) | | 3, 4, 5, 18 |
| 20 | 20.5 ($CH_3$) | 1.06 (3H, s) | | 1, 5, 9, 10 |
| $CH_3COO$ | 21.1 ($CH_3$) | 2.06 (3H, s) | | $CH_3COO$ |
| $CH_3COO$ | 169.6 ($C_{quat}$) | | | |

[a] in $CDCl_3$, [b] 101 MHz; [c] 600 MHz, ppm [integ., mult., J (Hz)]; ov—overlapping signals; m—complex multiplet.

4) Conversion of Membranolide (3) to the Corresponding Triol (20):

Scheme 6: reduction of membranolide (3) to produce the corresponding triol product (20)

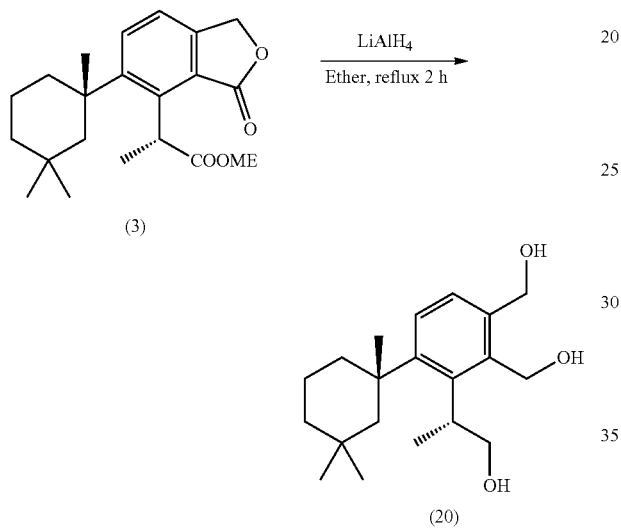

A solution of membranolide (3) (25 mg, 0.073 mmol) in dry ether (4.0 mL) was added to a stirred suspension of lithium aluminium hydride (25 mg, 0.66 mmol) in dry ether (5.0 mL) under an atmosphere of dry nitrogen. The mixture was heated under reflux for 2 h, cooled to 0° C., and quenched with ethyl acetate, followed by 2 M hydrochloric acid (3 mL). The mixture was extracted with ethyl acetate (3×15 mL), and the combined organic extracts were washed with dilute sodium bicarbonate solution (5 mL), dried over $Na_2SO_4$, and evaporated to give 32.5 mg of a crude oil. The oil was purified by NP-HPLC using a gradient (hexane: EtOAc, (0:1-1:0, v/v)). The compound obtained was not pure enough and an extra analytical HPLC separation was therefore required to give approx. 1 mg of the pure triol. (20) (0.9 mg, 0.003 mmol, 4%): HRESIMS m/z 343.224 [M+Na]+ 343.224 calculated for $C_{20}H_{36}O_3Na$. $^1$H-NMR and $^{13}C$ NMR data see Table 11. This semi-synthetic derivative was first published by Molinski and Faulkner in 1987[1]

TABLE 11

NMR Data of triol derivative (20)

| | $\delta_H^c$ |
|---|---|
| 1α | 1.49 (1H, ov m) |
| β | 2.28 (1H, br dt, 14.2, ≈2.5) |
| 2α | 1.63 (1H, m) |

TABLE 11-continued

NMR Data of triol derivative (20)

| | $\delta_H^c$ |
|---|---|
| β | 1.78 (1H, m) |
| 3 | 1.28 (2H, ov m) |
| 5α | 1.48 (1H, ov d, 14.1) |
| β | 2.17 (1H, br d, 14.1) |
| 6α | 4.88 (1H, dd, 11.1, 7.6) |
| β | 4.62 (1H, dd, 11.1, 8.5) |
| 7 | 4.15 (1H, m,) |
| 11 | 7.45 (1H, d, 8.3) |
| 12 | 7.18 (1H, d, 8.3) |
| 15α | 4.91 (1H, d, 12.6) |
| β | 4.83 (1H, d, 12.6) |
| 16α | 4.88 (1H, d, 11.9) |
| β | 4.62 (1H, d, 11.9) |
| 17 | 1.46 (3H, d, 7.2) |
| 18 | 0.38 (3H, s) |
| 19 | 0.91 (3H, s) |
| 20 | 1.44 (3H, s) |
| OH | 2.60 (3H, br s) |

[a] in $CDCl_3$, [c] 400 MHz, ppm [integ., mult., J (Hz)]; ov—overlapping signals; m—complex multiplet.

Scheme 7: Glaciolan derviatives

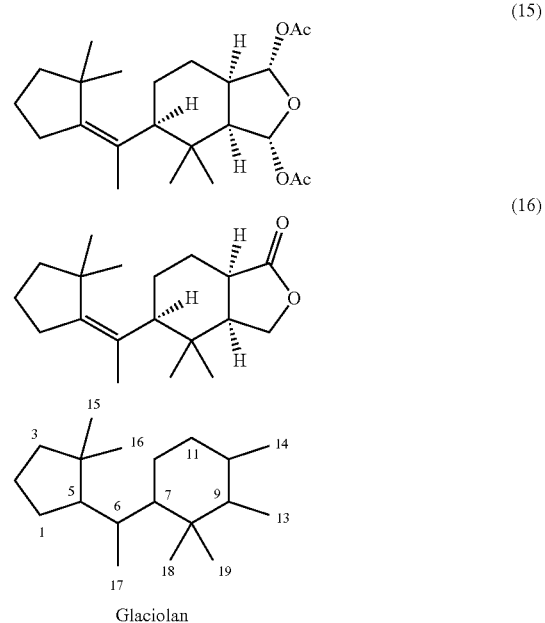

Glaciolan

Note that the original numbering system found in literature for (15)[10] and glaciolide (16)[11] were different. The chosen system is accorded to Tischler et al 1989. Norditerpene (15) was obtained as a clear oil. HRESIMS m/z 415.245 [M+Na]+ 415.246 calculated for $C_{23}H_{36}O_5Na$. $^1$H-NMR and $^{13}$C NMR data see Table 12.

TABLE 12

NMR Data of Norditerpene (15)

| | $\delta_H{}^c$ |
|---|---|
| 1α | 2.18 (1H, m) |
| β | 2.29 (1H, m) |
| 2 | 1.55 (2H, ov m) |
| 3 | 1.55 (2H, ov m) |
| 7 | 2.45 (1H, bdd, 11.1, 2.0) |
| 9 | 2.03 (1H, d, 7.6) |
| 10 | 2.66 (1H, dddd, 7.6, 7.3, 1.6) |
| 11α | 1.74 (1H, ov m) |
| β | 1.82 (1H, ov m) |
| 12α | 1.26 (1H, m) |
| β | 1.78 (1H, ov m) |
| 13 | 6.18 (1H, s) |
| 14 | 6.14 (1H, d, 7.3) |
| 15 | 1.15 (3H, s) |
| 16 | 1.23 (3H, s) |
| 17 | 1.51 (3H, br s) |
| 18 | 1.02 (3H, s) |
| 19 | 1.03 (3H, s) |
| OAc | 2.07 & 2.11 (2 × 3H, s) |

$^a$in CDCl$_3$, $^c$600 MHz, ppm [integ., mult., J (Hz)]; ov—overlapping signals; m—complex multiplet.

Glaciolide (16) was obtained as a clear oil. HRESIMS m/z 291.232 [M+H]+. 291.232 calculated for $C_{19}H_{31}O_2$. $^1$H-NMR and $^{13}$C NMR spectrum see (Table 13).

TABLE 13

NMR Data of Glaciolide (16)

| | $\delta_H{}^c$ |
|---|---|
| 1 | 2.17-2.30 (2H, ov m) |
| 2 | 1.55 (2H, ov m) |
| 3 | 1.53 (2H, ov m) |
| 7 | 4.48 (1H, bdd, 12.0, 2.2) |
| 9 | 2.23 (1H, dd, 7.6, 5.4) |
| 10 | 2.63 (1H, bt, 7.7) |
| 11α | 1.77 (1H, ov m) |
| β (eq) | 2.28 (1H, brd, 9.2) |
| 12α | 1.79 (1H, ov m) |
| β | 1.26 (1H, ov m) |
| 13α | 4.15 (1H, dd, 9.8, 5.3) |
| β | 4.26 (1H, d, 9.8) |
| 15 | 1.17 (3H, s) |
| 16 | 1.23 (3H, s) |
| 17 | 1.49 (3H, t, 1.3) |

TABLE 13-continued

NMR Data of Glaciolide (16)

| | $\delta_H{}^c$ |
|---|---|
| 18 | 0.93 (3H, s) |
| 19 | 0.91 (3H, s) |

$^a$in CDCl$_3$, $^c$600 MHz, ppm [integ., mult., J (Hz)]; ov—overlapping signals; m—complex multiplet.

Scheme 8: Comparison of new norditerpene (17) with a structure already published[12] and the corresponding gracilan skeleton.

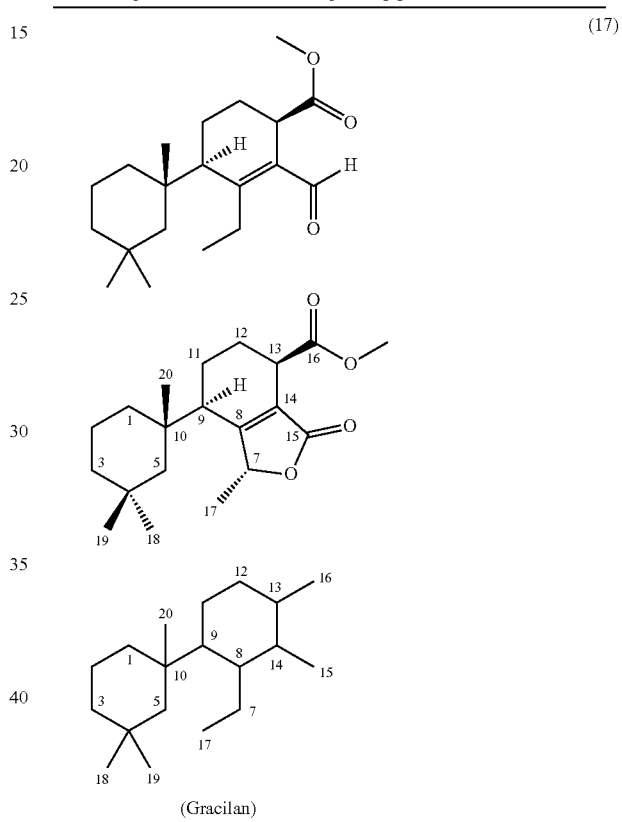

(Gracilan)

The new norditerpene (17) was obtained as a clear oil. HRESIMS m/z 343.2242 [M+Na]+ 343.2244 calculated for $C_{20}H_{32}O_3Na$.

TABLE 14

NMR Data of new norditerpene product (17)

| | $\delta_C{}^b$ (APT + gHSQCAD) | $\delta_H{}^c$ | COSY | HMBC |
|---|---|---|---|---|
| 1α | 37.7 (CH$_2$) | 1.42 (1H, m) | | |
| β | | 1.35 (1H, m) | | |
| 2 | 19.6 (CH$_2$) | 1.50-1.59 (2H, m) | | |
| 3α | 39.1 (CH$_2$) | 1.11 (1H, ov m) | | |
| β | | 1.35 (1H, ov m) | | |
| 4 | 31.3 (C$_{quat}$) | — | | |
| 5α | 52.6 (CH$_2$) | 1.46 (1H, ov d, 13.5) | | |
| β | | 1.35 (1H, ov d, 13.5) | | |
| 7α | 26.7 (CH$_2$) | 3.20 (1H, dq, 13.8, 7.3) | H-7β, H$_3$-17 | 8, 9, 14, 17 |
| β | | 2.43 (1H, dq, 13.8, 7.3) | H-7α, H$_3$-17 | |
| 8 | 167.9 (C$_{quat}$) | | | |
| 9 | 50.1 (CH) | 2.29 (1H, br t, 4.3) | | 5, 7, 8, 11, 12, 13, 14 |
| 10 | 39.5 (C$_{quat}$) | | | |

TABLE 14-continued

NMR Data of new norditerpene product (17)

| | $\delta_C{}^b$ (APT + gHSQCAD) | $\delta_H{}^c$ | COSY | HMBC |
|---|---|---|---|---|
| 11α | 24.5 (CH$_2$) | 2.01 (1H, dm, 14.0) | H-11β, H-9 | |
| β | | 1.40 (1H, ov m) | H-11α, H-9 | |
| 12α | 23.5 (CH$_2$) | 1.95-1.88 (1H, m) | | |
| β | | 1.85-1.78 (1H, m) | | 9 |
| 13 | 39.4 (CH) | 3.60 (1H, t, 7.9) | H-12 | 8, 14, 12 |
| 14 | 134.2 (C$_{quat}$) | 3.08 (1H, dd, 7.0, 8.0) | H-15, H-13 | |
| 15 | 190.5 (CH) | 10.18 (1H, s) | | 13, 14 |
| 16 | 174.8 (C$_{quat}$) | | | |
| 17 | 16.6 (CH$_3$) | 1.13 (3H, br t, 7.5) | | 8, 7 |
| 18 | 28.9 (CH$_3$) | 0.98 (3H, s) | | 3, 4, 5, 19 |
| 19 | 34.6 (CH$_3$) | 0.92 (3H, s) | | 3, 4, 5, 18 |
| 20 | 24.6 (CH$_3$) | 1.03 (3H, s) | | 1, 5, 9, 10 |
| CH$_3$O | 51.8 (CH$_3$) | 3.65 (3H, s) | | 16 |

$^a$in CDCl$_3$, $^b$101 MHz; $^c$600 MHz, ppm [integ., mult., J (Hz)]; ov—overlapping signals; m—complex multiplet.

REFERENCES FOR EXAMPLE 3

(1) Molinski, T. F.; Faulkner, D. J. Metabolites of the Antarctic Sponge *Dendrilla membranosa*. *J. Org. Chem.* 1987, 52 (2), 296-298.
(2) Pellaud, S.; Bory, A.; Chabert, V.; Romanens, J.; Chaisse-Leal, L.; Doan, A. V.; Frey, L.; Gust, A.; Fromm, K. M.; Mene-Saffrané, L. WRINKLED1 and ACYL-COA:DIACYLGLYCEROL ACYLTRANSFERASE1 Regulate Tocochromanol Metabolism in *Arabidopsis*. *New Phytol.* 2018, 217 (1), 245-260.
(3) Baker, B. J.; Kopitzke, R. W.; Yoshida, W. Y.; McClintock, J. B. Chemical and Ecological Studies of the Antarctic Sponge *Dendrilla membranosa*. *J. Nat. Prod.* 1995, 58 (9), 1459-1462.
(4) Graham, S. K.; Garson, M. J.; Bernhardt, P. V. The Absolute Structure of (+)-Aplysulfurin. *J. Chem. Crystallogr.* 2010, 40 (5), 468-471.
(5) Karuso, P.; Skelton, B. W.; Taylor, W. C.; White, A. H. The Constituents of Marine Sponges. I. The Isolation from *Aplysilla sulphurea* (Dendroceratida) of (1R*, 1'S*, 1'R*,3R*)-1-Acetoxy-4-Ethyl-5-(1,3,3-Trimethylcyclohexyl)-1,3-Dihydroisobenzofuran-1'(4),3-Carbolactone and the Determination of Its Crystal Structure. *Aust. J. Chem.* 1984, 37 (5), 1081-1093.
(6) Karuso, P.; Bergquist, P. R.; Cambie, R. C.; Buckleton, J. S.; Clark, G. R.; Rickard, C. E. F. Terpenoid Constituents of Morphologically Similar Sponges in the Family Aplysillidae. *Aust. J. Chem.* 1986, 39 (10), 1643-1653.
(7) Buckleton, J. S.; Bergquist, P. R.; Cambie, R. C.; Clark, G. R.; Karuso, P.; Rickard, C. E. F. Structure of Tetrahydroaplysulphurin-1. *Acta Crystallogr.* C 1987, 43 (12), 2430-2432.
(8) Keyzers, R. A.; Northcote, P. T.; Zubkov, O. A. Novel Anti-Inflammatory Spongian Diterpenes from the New Zealand Marine Sponge *Chelonaplysilla violacea*. *Eur. J. Org. Chem.* 2004, 2004 (2), 419-425.
(9) Ankisetty, S.; Amsler, C. D.; McClintock, J. B.; Baker, B. J. Further Membranolide Diterpenes from the Antarctic Sponge *Dendrilla membranosa*. *J. Nat. Prod.* 2004, 67 (7), 1172-1174.
(10) Mayol, L.; Piccialli, V.; Sica, D. New Degraded Diterpenes from the Sponge *Spongionella gracilis*. *Gazzetta Chim. Ital.* 1988, 118, 559-563.
(11) Tischler, M.; Andersen, R. J. Glaciolide, a Degraded Diterpenoid with a New Carbon Skeleton from the Nudibranch *Cadlina luteomarginata* and the Sponge *Aplysilla glacialis*. *Tetrahedron Lett.* 1989, 30 (42), 5717-5720.
(12) Diaz-Marrero, A. R.; Dorta, E.; Cueto, M.; San-Martín, A.; Darias, J. Conformational Analysis and Absolute Stereochemistry of 'Spongian'-Related Metabolites. *Tetrahedron* 2004, 60 (5), 1073-1078.

Example 4

Compound Characteristics

| Compound | Common Name (Abbreviation) | Chemical Formula | Molecular Wt. (g/mol) | Cytotoxicity (µM) against strain J774A.1 |
|---|---|---|---|---|
| 1 | aplysulphurin (AS) | $C_{22}H_{28}O_5$ | 372.4610 | 12.3 |
| 2 | tetrahydroaplysulphurin (THAS) | $C_{22}H_{32}O_5$ | 376.4930 | >133 |
| 3 | membranolide (mem-1) | $C_{21}H_{28}O_4$ | 344.4510 | 76.8 |
| 4 | tetrahydromembranolide (THM-1) | $C_{21}H_{32}O_4$ | 348.4830 | 64.9 |
| 5 | membranoid A (Mem-A) | $C_{21}H_{28}O_4$ | 344.4510 | 54.6 |
| 6 | membranoid B (Mem-B) | $C_{22}H_{32}O_5$ | 376.4930 | >133 |
| 7 | membranoid C (Mem-C) | $C_{22}H_{32}O_5$ | 376.4930 | >133 |
| 8 | membranoid D (Mem-D) | $C_{22}H_{32}O_5$ | 376.4930 | >133 |
| 9 | membranoid E (Mem-E) | $C_{22}H_{32}O_5$ | 376.4930 | 95 |
| 10 | membranoid G (Mem-G) | $C_{20}H_{26}O_4$ | 330.4240 | >151 |
| 11 | membranoid X (Mem-X) | $C_{23}H_{32}O_6$ | 404.503 | 62.9 |
| 12 | membranoid Y (Mem-Y) | $C_{21}H_{28}O_5$ | 360.4500 | >139 |
| 13 | 9, 11-dihydrogracilin A (DHG) | $C_{23}H_{36}O_5$ | 392.5360 | ND |
| 14 | Cadlinolide C (CAD-C) | $C_{20}H_{30}O_3$ | 318.2195 | ND |
| 15 | Norditerpene I (NDT-1) | $C_{23}H_{36}O_5$ | 392.5360 | ND |
| 16 | Glaciolide (GLL) | $C_{19}H_{30}O_2$ | 290.4417 | ND |
| 17 | ABO-1 | $C_{20}H_{32}O_3$ | 320.473 | ND |
| 18 | Tetrahydroaplytrioxolane (ABO-2) | $C_{22}H_{32}O_8$ | 424.49 | ND |
| 19 | keto-9, 11-dihydrogracilin A (K-DHG) | $C_{21}H_{32}O_6$ | 380.481 | ND |
| 20 | Mebranolide triol (Mem-1-T) | $C_{20}H_{32}O_3$ | 320.4730 | ND |

-continued

| Compound | Common Name (Abbreviation) | Chemical Formula | Molecular Wt. (g/mol) | Cytotoxicity (μM) against strain J774A.1 |
|---|---|---|---|---|
| 21 | Dendrillin (DNDL) | $C_{23}H_{36}O_6$ | 408.2512 | ND |
| 22 | Membranoid F | $C_{21}H_{28}O_5$ | 360.4500 | ND |
| 23 | PSC16-30-A-(25-26)-k | $C_{20}H_{24}O_4$ | 328.4080 | ND |
| 24 | Darwinolide | $C_{22}H_{32}O_5$ | 376.4930 | 20.13 |
|  | PSC17-16-A-b | $C_{20}H_{32}O_3$ | 320.4730 | ND |
|  | ABO-3 | ND | ND | ND |
|  | ABO-4 | ND | ND | ND |

We claim:

1. A method of treating a biofilm in a subject or preventing the formation of a biofilm in a subject, the method comprising administering to the subject an effective amount of a compound having the formula:

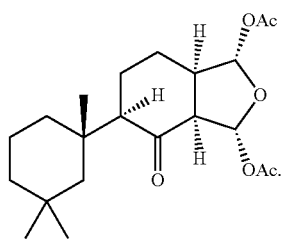

2. The method of claim 1, wherein the compound is administered to the subject as a unit dose composition comprising a pharmaceutically acceptable carrier.

3. The method of claim 1, wherein the compound is administered to the subject at a dosage of from about 0.1 μg/kg to about 1,000 μg/kg per unit dose composition.

4. The method of claim 1, wherein the compound has a $MBEC_{90}$ value less than or equal to 100 μg/ml against methicillin-resistant *Staphylococcus aureus* (MRSA).

5. The method of claim 1, wherein the biofilm comprises methicillin-resistant *Staphylococcus aureus* (MRSA).

6. The method of claim 1, wherein the biofilm comprises multi-drug resistant *A. baumannii*.

* * * * *